US012758119B2

(12) United States Patent
Jalde

(10) Patent No.: US 12,758,119 B2
(45) Date of Patent: Oct. 13, 2026

(54) EVENT-BASED MEDICAL DECISION SUPPORT SYSTEM

(71) Applicant: MAQUET CRITICAL CARE AB, Solna (SE)

(72) Inventor: Fredrik Jalde, Sundbyberg (SE)

(73) Assignee: MAQUET CRITICAL CARE AB, Solna (SE)

( * ) Notice: Subject to any disclaimer, the term of this patent is extended or adjusted under 35 U.S.C. 154(b) by 354 days.

(21) Appl. No.: 17/250,898

(22) PCT Filed: Oct. 3, 2019

(86) PCT No.: PCT/SE2019/050958
§ 371 (c)(1),
(2) Date: Mar. 22, 2021

(87) PCT Pub. No.: WO2020/071990
PCT Pub. Date: Apr. 9, 2020

(65) Prior Publication Data

US 2022/0000390 A1 Jan. 6, 2022

(30) Foreign Application Priority Data

Oct. 3, 2018 (SE) .................................. 1851191-5

(51) Int. Cl.
*A61B 5/08* (2006.01)
*A61B 5/00* (2006.01)
(Continued)

(52) U.S. Cl.
CPC .......... *A61B 5/0826* (2013.01); *A61B 5/0205* (2013.01); *A61B 5/14542* (2013.01);
(Continued)

(58) Field of Classification Search
CPC . A61B 5/0826; A61B 5/0205; A61B 5/14542; A61B 5/742; A61B 2562/0247;
(Continued)

(56) References Cited

U.S. PATENT DOCUMENTS

| | | | |
|---|---|---|---|
| 5,447,164 | A | 9/1995 | Shaya et al. |
| 5,860,918 | A | 1/1999 | Schradi et al. |

(Continued)

FOREIGN PATENT DOCUMENTS

| | | |
|---|---|---|
| CN | 108135534 | 6/2018 |
| WO | 2011/116340 | 9/2011 |

(Continued)

OTHER PUBLICATIONS

Joshi et al., "Pattern discovery in critical alarms originating from neonates under intensive care", Institute of Physics and Engineering in Medicine: Physiological Measurement, vol. 37, No. 4, Mar. 2016, 17 sheets.

(Continued)

*Primary Examiner* — Puya Agahi
(74) *Attorney, Agent, or Firm* — Fay Kaplun & Marcin, LLP

(57) ABSTRACT

A clinical decision support system for supporting a clinician in decisions relating to a patient is disclosed. The system may include at least one computer performing an event correlation trend analysis based on physiological parameters obtained from the patient. The computer is configured to perform the analysis by: identifying occurrences of a primary physiological event; identifying occurrences of at least one secondary physiological event that is physiologically linked to the primary physiological event; establishing a trend of correlation between the primary physiological event and the at least one secondary physiological event; and
(Continued)

presenting event correlation trend data indicative of the trend on a display of the clinical decision support system.

21 Claims, 7 Drawing Sheets

(51) Int. Cl.
*A61B 5/0205* (2006.01)
*A61B 5/145* (2006.01)
*G16H 20/40* (2018.01)
*G16H 40/63* (2018.01)
*G16H 50/20* (2018.01)

(52) U.S. Cl.
CPC ............. *A61B 5/742* (2013.01); *G16H 20/40* (2018.01); *G16H 40/63* (2018.01); *G16H 50/20* (2018.01); *A61B 2562/0247* (2013.01)

(58) Field of Classification Search
CPC .......... A61B 5/02; G16H 20/40; G16H 40/63; G16H 50/20
See application file for complete search history.

(56) References Cited

U.S. PATENT DOCUMENTS

| | | | | |
|---|---|---|---|---|
| 2003/0060725 | A1* | 3/2003 | Kline ..................... | A61B 5/417 600/529 |
| 2005/0115561 | A1 | 6/2005 | Stahmann et al. | |
| 2005/0234313 | A1 | 10/2005 | Rowlandson et al. | |
| 2005/0234355 | A1 | 10/2005 | Rowlandson | |
| 2007/0000494 | A1* | 1/2007 | Banner ................ | A61B 5/0205 128/204.23 |
| 2007/0191697 | A1 | 8/2007 | Lynn et al. | |
| 2011/0046498 | A1 | 2/2011 | Klap et al. | |
| 2011/0061647 | A1 | 3/2011 | Stahmann et al. | |
| 2012/0216811 | A1* | 8/2012 | Kimm .................... | G16H 20/40 128/204.23 |
| 2012/0310100 | A1* | 12/2012 | Galen .................. | A61B 5/7282 600/500 |
| 2013/0211206 | A1 | 8/2013 | Sand et al. | |
| 2014/0052007 | A1 | 2/2014 | Mcgregor et al. | |
| 2014/0163897 | A1 | 6/2014 | Lynn et al. | |
| 2015/0216447 | A1* | 8/2015 | Colman ............... | A61B 5/7275 600/532 |
| 2016/0287170 | A1 | 10/2016 | Ronen et al. | |
| 2017/0053084 | A1 | 2/2017 | McMahon et al. | |

FOREIGN PATENT DOCUMENTS

| | | |
|---|---|---|
| WO | 2013/033655 | 3/2013 |
| WO | 2018/085563 | 5/2018 |

OTHER PUBLICATIONS

Truong, "Predicting Adverse Outcomes in Preterm Infants using Early Bedside Monitoring Data", A thesis submitted in partial fulfillment of the requirements for the degree of Bachelor of Science in Physics from the College of William and Mary, May 2, 2018, 26 sheets.

* cited by examiner

51

| | TW1 | TW2 | TW3 | TW4 | TW5 | TW6 | TW7 | TW8 | TW9 | TW10 | TW11 | ... |
|---|---|---|---|---|---|---|---|---|---|---|---|---|
| Only apnea | 22 | 18 | 20 | 20 | 13 | 19 | 13 | 13 | 13 | 8 | 8 | ... |
| Bradycardia | 0 | 0 | 0 | 0 | 0 | 0 | 5 | 5 | 0 | 0 | 0 | ... |
| Desaturation | 66 | 9 | 7 | 7 | 0 | 0 | 20 | 0 | 0 | 0 | 0 | ... |
| Brady & desat | 0 | 0 | 6 | 6 | 6 | 0 | 0 | 7 | 0 | 0 | 0 | ... |

EVENT-BASED MEDICAL DECISION SUPPORT SYSTEM

TECHNICAL FIELD

The present disclosure relates to the field of medical monitoring systems and, in particular, to a system, a method, and a computer program for supporting a clinician in decisions relating to medical treatment of a patient.

BACKGROUND

In most clinical situations, it is important to monitor the physiological state of the patient. There are numerous vital signs and physiological parameters that may be monitored in different ways in different clinical situations in order to support medical personnel in the assessment of the physiological state of the patient.

In the assessment of the physiological state of the patient, it may also be important to monitor occurrences and effects of certain physiological events. For example, in patients suffering from apnea, it is important to monitor the occurrence of apnoeic events and the physiological effect of the apnea on the patient. If, for instance, the apnoeic event causes oxygen desaturation and/or bradycardia in the patient, trained medical personnel may conclude that the apnea is severe and the physiological state of the patient is impaired. If, on the other hand, the detected apnoeic event does not cause any oxygen desaturation or bradycardia in the patient, it may be concluded that the apnea is a non-severe type of apnea that does not adversely affect the physiological state of the patient.

An example of a clinical situation where it is important to monitor apnea and other physiological events, and the effects of the physiological events on the patient, is during mechanical ventilation.

U.S. Pat. No. 5,447,164 A discloses an interactive medical information display system that may be used for clinical decision support. The system acquires physiological parameters from a patient and stores the parameters in a real-time database. A user (e.g., a clinician) may define various event types that are to be identified from the acquired physiological parameters. The identified event occurrences are then displayed to the user.

This type of medical information display system may be used to assist the clinician in identification of correlated physiological events, thereby facilitating the assessment of the physiological state of the ventilated patient. Given the example of apnea discussed above, the system may assist the clinician in identifying apnoeic events causing oxygen desaturation and/or bradycardia in the patient, and may thus facilitate the manual task of classifying the apnea to gain more knowledge on the physiological state of the patient.

However, there is a need for a more refined clinical decision support system that further facilitates the assessment of the physiological state of a patient.

SUMMARY

The present disclosure relates to a system, a method and a computer program which may facilitate clinical decision making in relation to medical treatment of a patient.

In addition, the present disclosure relates to a system, a method and a computer program which may facilitate clinical decision making in relation to mechanically ventilated patients.

Furthermore, the present disclosure relates to a system, a method and a computer program which may facilitate the assessment of the physiological state of a mechanically ventilated patient.

Also, the present disclosure relates to a system, a method and a computer program which may allow clinically potentially important information on occurrences of physiological events to be presented to medical personnel in an intuitive and easily comprehensible manner.

The present disclosure relies on the realisation that in many clinical situations, the trend (i.e., the change over time) of a correlation between different physiological events is a valuable input parameter in the assessment of the physiological state of a patient.

Therefore, according to one aspect of the present disclosure, there is provided a clinical decision support system for supporting a clinician in decisions relating to a patient. The system comprises at least one computer for performing an event correlation trend analysis based on physiological parameters obtained from the patient. The at least one computer is configured to perform the event correlation trend analysis by: identifying occurrences of a primary physiological event; identifying occurrences of at least one secondary physiological event that is physiologically linked to the primary physiological event; establishing a trend of a correlation between the primary physiological event and the at least one secondary physiological event, and presenting event correlation trend data indicative of said trend on a display of the clinical decision support system.

By presenting the event correlation trend data to the clinician, the clinician can use the data to make clinical decisions based on the trend of correlation between two or more physiologically linked events. In particular, the clinician can use the trend of correlation between physiologically linked events in the assessment of the physiological state of the patient.

The system may be configured to identify several different types of secondary physiological events, and to establish and present a trend of correlation between the primary physiological event and each of the secondary physiological event types. For example, the primary physiological event may be apnea (i.e., an apnoeic event), a first type of secondary physiological event may be bradycardia, and a second type of secondary physiological event may be oxygen desaturation. In this way, a bigger and even more relevant clinical picture can be provided to the clinician. If, for instance, both the trend of correlation between apnea and bradycardia and the trend of correlation between apnea and oxygen desaturation are decreasing, the clinician may conclude that the physiological state of the patient is improving. If the trends have reached a level at which there is no or nearly no correlation between apnea and any of bradycardia or oxygen desaturation, the clinician may conclude that the apnea does not severely affect the physiological state of the patient, and that no treatment or no further treatment of the patient is required. If, for example, the patient is connected to a breathing apparatus providing mechanical ventilation to the patient, the clinician may, in this instance, conclude that the patient may be subject to weaning from mechanical ventilation.

The system may comprise various sensors for measuring physiological parameters from which the occurrences of the primary and the at least one secondary physiological events can be identified. For example, the system may comprise a respiratory sensor, e.g., a flow sensor, a pressure sensor or an Edi sensor, that obtains respiratory activity data from the patient and which is operably connected to send the respiratory activity data to the at least one computer. The computer may be configured to identify apnea based on the received respiratory activity data. The system may also comprise a heart rate sensor, e.g., an electrocardiogram (ECG) sensor, an Edi sensor or a pulse oximeter, that obtains heart rate data from the patient and that is operably connected to send the heart rate data to the at least one computer. The computer may be configured to identify bradycardia based on the received heart rate data. The system may also comprise a blood oxygen sensor, e.g., a pulse oximeter, that obtains blood oxygen saturation data from the patient and that is operably connected to send the blood oxygen saturation data to the at least one computer. The computer may be configured to identify oxygen desaturation based on the received blood oxygenation data.

Thus, according to one aspect of the present disclosure, there is provided a clinical decision support system for supporting a clinician in decisions relating to a patient. The system comprises at least one computer configured to perform an event correlation trend analysis based on physiological parameters obtained from the patient, and a display that is operably connected to the at least one computer. The system further comprises a first and at least a second sensor for measuring the physiological parameters, selected from the group consisting of: a respiratory sensor that obtains respiratory activity data from the patient and that is operably connected to send the respiratory activity data to the at least one computer; a heart rate sensor that obtains heart rate data from the patient and that is operably connected to send the heart rate data to the at least one computer; and a blood oxygen sensor that obtains blood oxygen saturation data from the patient and that is operably connected to send the blood oxygen saturation data to the at least one computer. The at least one computer is configured to perform the event correlation trend analysis by identifying occurrences of a primary physiological event based on the data received from the first sensor, identifying occurrences of at least one secondary physiological event that is physiologically linked to the primary physiological event, wherein the occurrences of the at least one secondary event are identified based on the data received from the at least second sensor, establishing a trend of a correlation between the primary physiological event and the at least one secondary physiological event, and presenting event correlation trend data indicative of the trend on the display of the clinical decision support system.

The physiological parameters may be obtained during any type of medical treatment in order to visualise trends of correlation between different physiological events, which trends may support medical personnel in decisions relating to the treatment. The event correlation trend analysis may also be performed for patients that are not undergoing any medical treatment at all, whereby the trends of correlation between the physiological events may indicate whether or not the patient is in need of medical treatment.

For instance, the physiological parameters may be obtained during respiratory treatment in the form of mechanical ventilation therapy, continuous positive airway pressure (CPAP) therapy or oxygen flow therapy, e.g., supplemental oxygen therapy or high-flow oxygen therapy.

The computer may be configured to establish the correlation trend by categorising identified primary physiological events based on the types of physiologically linked secondary physiological events, and determining the number of primary physiological events of each category as a function of time. The computer may also be configured to categorise identified primary physiological events that are not physiologically linked to any secondary physiological event into a specific category.

In an exemplary embodiment, the computer may be configured to establish the correlation trend by determining, for each of a plurality of discrete time windows, the number of primary physiological events in each category.

The result of the determination for each time window may, for instance, be a number of primary physiological events (e.g., apnea) of a first category, which primary physiological events are not physiologically linked to any secondary physiological event; a number of primary physiological events of a second category, which primary physiological events are physiologically linked to a first type of secondary physiological event (e.g., bradycardia); a number of primary physiological events of a third category, which primary physiological events are physiologically linked to a second type of secondary physiological events (e.g., oxygen desaturation), and a number of primary physiological events of a fourth category, which primary physiological events are physiologically linked to both the first type of secondary physiological events and the second type of secondary physiological events.

In this way, the primary physiological events may be categorised into different categories depending on whether they are physiologically linked to one or more secondary physiological events, and depending on the type of any physiologically linked secondary physiological event. The trend of correlation between the primary physiological event and any secondary physiological event may then be established by determining the number of primary physiological events of the relevant category in different time windows. In this case, the time step or resolution of the correlation trend analysis performed by the computer corresponds to the length of the time window.

Consequently, the clinical decision support system could also be described as a clinical decision support system for supporting a clinician in decisions relating to a patient, comprising at least one computer for performing an event correlation trend analysis based on physiological parameters obtained from the patient, where the computer is configured to perform said analysis by: identifying occurrences of a primary physiological event; identifying occurrences of at least one secondary physiological event that is physiologically linked to the primary physiological event; categorising primary physiological events based on the types of physiologically linked secondary physiological events, and presenting a number or distribution of primary physiological events of each category as a function of time.

The data representing the number or distribution of primary physiological events of each category as a function of time constitute event correlation trend data indicative of the trend of correlation between the primary physiological event and the at least one secondary physiological event.

The event correlation trend data may be presented in any way as long as the data visualises any change over time in correlation between the primary physiological event and the at least one secondary physiological event.

In one example, the event correlation data is presented as a data table listing the numbers of primary physiological events of each category for different time windows. In this case, the table should be properly sorted to clearly visualise the correlation trend between the primary physiological event and the at least one type of secondary physiological event.

Preferably, however, the event correlation data is presented in form of an event correlation trend plot including at least one graph clearly visualising the trend of correlation between the primary physiological event and the at least one type of secondary physiological event. The event correlation trend plot may be displayed in a correlation trend pane on the display. The computer may further be configured to present occurrences of the primary physiological event and occurrences of the at least one secondary physiological event on the display, for example in an event tracking pane that may be disposed together with the correlation trend pane within a selectable trend evaluation view that is viewable on the display.

In one exemplary embodiment, the event correlation trend plot comprises a graph representing the correlation between the primary physiological parameter and the at least one secondary physiological parameter. The curve may represent the number of primary physiological events of a specific category as a function of time, e.g., the number of primary physiological events of a specific category identified in the respective time window. Preferably, the event correlation trend plot comprise one such graph for each category of primary physiological events.

In case there are multiple categories of primary physiological events, the event correlation trend plot may be a single plot comprising multiple graphs, e.g., one graph for each category of primary physiological events. In this case, the graphs may be distribution graphs representing the distribution of different categories of primary physiological events as a function of time. Using graphs representing the distribution rather than the actual number of primary physiological events in each category as a function of time may be advantageous in that the visualisation of the trend for each category becomes clearer and more easily comprehensible.

The primary physiological event and the one or more secondary physiological events to be subject to the event correlation trend analysis may be predetermined or selectable by a user of the clinical decision support system. The clinical decision support system may comprise one or more predetermined groups of events and be configured to prompt the user to select a group of events for which the event correlation trend analysis is to be performed. The clinical decision support system may also be configured to prompt the user to indicate two or more separate events for which the correlation trend analysis is to be performed. The system may further be configured to prompt the user to select which event should be considered the primary physiological event and which event or events should be considered a secondary physiological event.

The primary physiological event and/or the at least one secondary physiological event may be either predefined by the clinical decision support system or defined by the user.

The proposed event correlation trend analysis is not limited to any particular type of events. However, in order for the event correlation trend analysis to be meaningful, the at least one secondary physiological event should be physiologically linked to the primary physiological event. To this end, the clinical decision support system may be configured to determine, for each identified primary physiological event, whether there is at least one secondary physiological event that is physiologically linked to the identified primary physiological event. The determination may be made based on a causal relationship between the primary physiological event and the at least one secondary physiological event. If there is a predefined causal relationship between the primary physiological event and the at least one secondary physiological event, the at least one secondary physiological event can be assumed to be physiologically linked to the primary physiological event.

According to one example, the events for which the correlation trend analysis is performed comprise at least two events selected from the group consisting of apnea, bradycardia and oxygen desaturation. In one exemplary embodiment, apnea may be the primary physiological event and bradycardia and/or oxygen desaturation may be the secondary physiological event(s). In another exemplary embodiment, bradycardia may be the primary physiological event and apnea and/or oxygen desaturation may be the secondary physiological event(s).

The system may further be configured to present one or more recommendations relating to a treatment of the patient, based on the established trend of correlation between the primary physiological event and the at least one secondary physiological event. The one or more recommendations may relate to an ongoing treatment, such as an ongoing respiratory treatment of the patient provided by a breathing apparatus to which the patient is connected, or relate to a not yet ongoing but recommended treatment of the patient. For instance, the one or more recommendations may comprise a recommendation to decrease or remove a ventilatory support provided to the patient by the breathing apparatus, i.e., a recommendation relating to weaning of patient from the breathing apparatus. Alternatively, the one or more recommendations may comprise a recommendation to start ventilating the patient using mechanical ventilation or to increase a ventilatory support provided to the patient by a breathing apparatus to which the patient is already connected. The one or more recommendations may even comprise a recommendation of settings for a medical device currently providing medical treatment to the patient. For instance, the one or more recommendations may comprise a recommendation on ventilator settings for a mechanical ventilator mechanically ventilating the patient.

The one or more recommendations are generated and caused to be presented to the clinician by the at least one computer of the clinical decision support system. The one or more recommendations may be presented to the clinician in any conceivable manner, e.g., visually and/or orally. For instance, the one or more recommendations may be presented on a display of the clinical decision support system.

The system may further be configured to automatically adjust the settings of a computerized medical device providing medical treatment to the patient, based on the established trend of correlation between the primary physiological event and the at least one secondary physiological event. In an exemplary embodiment wherein a breathing apparatus is providing respiratory treatment to the patient, the computer of the clinical decision support system may be configured to present a recommendation on adjusted settings for the breathing apparatus, e.g., settings affecting the level of ventilatory support provided to the patient by the breathing apparatus, based on the established trend of correlation, and to automatically adjust the breathing apparatus settings accordingly upon approval by the clinician, e.g., in response to the actuation of an acceptance button by the clinician. The system may also allow the clinician to modify one or more of the recommended adjusted settings for the breathing apparatus before approving the clinician modified version of the recommended settings by, for example, the clinician subsequently actuating an acceptance button that causes the system to accept and implement via the breathing apparatus the clinician modified version of the recommended settings.

The clinical decision support system may further comprise a hardware memory device in which the data obtained by the sensors of the system and pertaining to the physiological parameters of the patient are stored. Likewise, the system may be configured to store data pertaining to identified occurrences of the primary and the at least one secondary physiological event in the hardware memory device.

The clinical decision support system may, in some embodiments, be realized in form of a clinical monitoring system for monitoring multiple different types of physiological events and determining one or more correlations between different types of physiological events. The clinical decision support system may also be incorporated into or associated with a computerized medical device and configured to monitor the physiological state of a patient connected to the medical device and/or to provide recommendations related to a treatment of the patient provided by the medical device and/or to control the medical device, based on the established trend of correlation between the primary physiological event and the at least one secondary physiological event. For example, the clinical decision support system may be incorporated into or associated with a breathing apparatus for providing respiratory treatment to the patient.

Thus, according to one aspect of the present disclosure, there is provided a clinical monitoring system for monitoring multiple different types of physiological events and determining one or more correlations between different types of physiological events, wherein the clinical monitoring system comprises a clinical decision support system as described above. Consequently, the clinical monitoring system may comprise: at least one computer for performing an event correlation trend analysis based on physiological parameters obtained from the patient; a first and at least a second sensor selected from the group consisting of a respiratory sensor that obtains respiratory activity data from the patient and that is operably connected to send the respiratory activity data to the at least one computer, a heart rate sensor that obtains heart rate data from the patient and that is operably connected to send the heart rate data to the at least one computer, and a blood oxygen sensor that obtains blood oxygen saturation data from the patient and that is operably connected to send the blood oxygen saturation data to the at least one computer; and a display operably connected to the at least one computer, wherein the first and the at least second sensor are operably connected to the at least one computer, and the at least one computer is configured to perform the event correlation analysis by identifying occurrences of a primary physiological event based on the data received from the first sensor; identifying occurrences of at least one secondary physiological event that is physiologically linked to the primary physiological event, wherein occurrences of the at least one secondary physiological event are identified based on the data received from the at least second sensor; establishing a trend of correlation between the primary physiological event and the at least one secondary physiological event, and presenting event correlation trend data indicative of the trend on the display of the clinical monitoring system.

According to another aspect of the present disclosure, there is provided a ventilation system comprising a breathing apparatus for providing respiratory treatment to a patient, such as a mechanical ventilator, a CPAP machine or an oxygen flow device, and a clinical decision support system as described above, for monitoring physiological events and for supporting a clinician in decisions relating to the treated patient.

The clinical decision support system of the ventilation system may be separate from and operatively connected to the breathing apparatus. For example, the clinical decision support system may form part of a clinical monitoring system, as described above, which clinical monitoring system is operatively connected to the breathing apparatus in order to exchange information with the breathing apparatus and, optionally, in order to control the breathing apparatus based on physiological parameters obtained by sensors of the clinical monitoring system.

In other embodiments, the clinical decision support system may be incorporated into and form an integral part of the breathing apparatus, which, for instance, may be a mechanical ventilator.

Consequently, according to other aspects of the present disclosure, there is provided a breathing apparatus comprising a clinical decision support system as described above, for monitoring physiological events and for supporting a clinician in decisions relating to a patient ventilated by the breathing apparatus. The breathing apparatus comprises: at least one computer for performing an event correlation trend analysis based on physiological parameters obtained from the patient; a first and at least a second sensor selected from the group consisting of a respiratory sensor that obtains respiratory activity data from the patient and that is operably connected to send the respiratory activity data to the at least one computer, a heart rate sensor that obtains heart rate data from the patient and that is operably connected to send the heart rate data to the at least one computer, and a blood oxygen sensor that obtains blood oxygen saturation data from the patient and that is operably connected to send the blood oxygen saturation data to the at least one computer; wherein the first and the at least second sensor are operably connected to the at least one computer, and the at least one computer is configured to perform the event correlation analysis by identifying occurrences of a primary physiological event based on the data received from the first sensor; identifying occurrences of at least one secondary physiological event that is physiologically linked to the primary physiological event, wherein occurrences of the at least one secondary physiological event are identified based on the data received from the at least second sensor; establishing a trend of correlation between the primary physiological event and the at least one secondary physiological event, and presenting event correlation trend data indicative of the trend on a display operably connected to the at least one computer.

The clinical decision support system of any of the clinical monitoring system and the breathing apparatus may be devised and configured as described above. Consequently, the at least one computer of any of the clinical monitoring system and the breathing apparatus may be configured to identify several different types of secondary physiological events, and to establish and present a trend of correlation between the primary physiological event and each of the secondary physiological event types. Furthermore, the at least one computer may be configured to categorise identified primary physiological events based on the types of physiologically linked secondary physiological events, and to establish the correlation trend by determining the number of primary physiological events of each category as a function of time. Yet further, the at least one computer may be configured to determine the number of primary physiological events in each category for each of a plurality of discrete time windows. The at least one computer of any of the clinical monitoring system and the breathing apparatus may further be configured to present the event correlation trend data in the form of an event correlation trend plot comprising at least one graph illustrating the trend of correlation between the primary physiological event and the at least one secondary physiological event. The event correlation trend plot may comprise multiple graphs of different colours or patterns, each illustrating a trend of correlation between the primary physiological event and a respective type of secondary physiological event. The multiple graphs may be distribution graphs representing the distribution of different categories of primary physiological events as a function of time. The at least one computer of any of the clinical monitoring system and the breathing apparatus may, for instance, be configured to identify apnea as the primary physiological event, and to identify any or both of bradycardia and oxygen desaturation as the at least one secondary physiological event. Alternatively, the at least one computer may be configured to identify bradycardia as the primary physiological event, and to identify any or both of apnea and oxygen desaturation as the at least one secondary physiological event. The at least one computer of any of the clinical monitoring system and the breathing apparatus may be configured to obtain the physiological parameters during a period of medical treatment of the patient, e.g., during a period of respiratory treatment provided to the patient by a breathing apparatus in the form of a mechanical ventilator, a CPAP machine or a device for providing oxygen flow therapy to the patient. The at least one computer may further be configured to present a recommendation relating to the medical treatment of the patient on the display operably connected to the at least one computer. For example, the at least one computer may be configured to present a ventilation recommendation relating to a respiratory treatment of the patient to a clinician, based on the established trend of correlation between the primary physiological event and the at least one secondary physiological event, The respiratory treatment may include mechanical ventilation of the patient, provided by a breathing apparatus. The display on which the recommendation is presented may include an actuation button and one or more recommendation modification buttons, wherein the one or more ventilation recommendation buttons are actuatable to modify the ventilation recommendation, and the actuation button, when actuated, results in the at least one computer operating the breathing apparatus so as to ventilate the patient in accordance with the ventilation recommendation unless modified by the one or more ventilation recommendation buttons, in which case the actuation button, when actuated, results in the at least one computer operating the breathing apparatus in accordance with the modified ventilation recommendation. The respiratory sensor of any of the clinical monitoring system and the breathing apparatus may be selected from the group consisting of a flow sensor, a pressure sensor and an Edi sensor. The heart rate sensor of any of the clinical monitoring system and the breathing apparatus may be selected from the group consisting of an ECG sensor, an Edi sensor or a pulse oximeter. The blood oxygen sensor of any of the clinical monitoring system and the breathing apparatus may be a pulse oximeter. The at least one computer of any of the clinical monitoring system and the breathing apparatus may be configured to identify apnea based on the respiratory activity data received from the respiratory sensor, to identify bradycardia based on the heart rate data received from the heart rate sensor, and to identify oxygen desaturation based on the blood oxygenation data received from the blood oxygen sensor. Any of the clinical monitoring system and the breathing apparatus may further be configured to monitor physiological parameters and store data pertaining to the physiological parameters in a hardware memory device, and to monitor identified primary physiological events and identified secondary physiological events and store data pertaining to the identified primary physiological events and the identified secondary physiological events in the hardware memory device.

According to another aspect of the present disclosure, there is provided a method for supporting a clinician in decisions relating to a patient. The method comprises a step of performing an event correlation trend analysis based on physiological parameters obtained from the patient, wherein the correlation trend analysis is performed by: identifying occurrences of a primary physiological event; identifying occurrences of at least one secondary physiological event that is physiologically linked to the primary physiological event; establishing a trend of a correlation between the primary physiological event and the at least one secondary physiological event, and presenting event correlation trend data indicative of the trend on a display of a clinical decision support system.

The method may comprise the steps of identifying several different types of secondary physiological events, and establishing and presenting a trend of correlation between the primary physiological event and each of the secondary physiological event types.

The method may further comprise the steps of categorising identified primary physiological events based on the types of physiologically linked secondary physiological events, and establishing the correlation trend by determining the number of primary physiological events of each category as a function of time. The number of primary physiological events of each category may be determined for each of a plurality of discrete time windows.

The event correlation data may be presented in the form of an event correlation trend plot comprising at least one graph illustrating the trend of correlation between the primary physiological event and the at least one secondary physiological event. The event correlation trend plot may be displayed in real time on an electronic display and/or printed out as a hardcopy and/or stored in a non-transitory hardware memory device for later review as a printed out hardcopy or as an image displayed on the electronic display or some other electronic display.

The event correlation trend plot may comprise multiple graphs, each visualising the trend of correlation between the primary physiological event and a respective type of secondary physiological event. The multiple graphs may be distribution graphs representing the distribution of different categories of primary physiological events as a function of time. Each of these graphs may be displayed in real time on an electronic display and/or printed out as a hardcopy and/or stored in a non-transitory hardware memory device for later review as a printed out hardcopy or as an image displayed on the electronic display or some other electronic display.

The primary physiological event and the at least one secondary physiological event may be events selected from the group consisting of apnea, bradycardia and oxygen desaturation.

The physiological parameters may be obtained during a period of mechanical ventilation of the patient, in which case the method serves to provide decision support to a clinician in relation to mechanical ventilatory treatment of the patient.

The physiological parameters may also be obtained during other types of medical treatments. For instance, the physiological parameters may be obtained during respiratory treatments in the form of CPAP therapy or oxygen flow therapy, in which case the method may serve to provide decision support to a clinician in relation to the ongoing respiratory treatment of the patient.

The method may further comprise a step of presenting one or more recommendations relating to a treatment of the patient, based on the established trend of correlation between the primary physiological event and the at least one secondary physiological event.

The method may further comprise a step of automatically adjusting the settings of a computerized medical device, such as a breathing apparatus, providing medical treatment to the patient, based on the established trend of correlation between the primary physiological event and the at least one secondary physiological event.

Alternatively, the method may comprise, instead of the step of automatically adjusting the settings, a step of semi-automatically adjusting the settings of the computerized medical device. In this embodiment, the method further comprises a step of semiautomatically adjusting the settings of the computerized medical device, such as the breathing apparatus, by providing medical treatment to the patient based on the established trend of correlation between the primary physiological event and the at least one secondary physiological event, wherein semiautomatic adjustment of settings involves providing recommended adjusted settings for the breathing apparatus that are implemented after activating an acceptance button and/or providing recommended adjusted settings that a clinician may modify before accepting via activation of the acceptance button so that the implemented adjusted settings are clinician modified recommended adjusted settings.

As understood from the above, the method is typically a computer-implemented method that is performed by the at least one computer of the clinical decision support system upon execution of a computer program.

Consequently, according to yet another aspect of the present disclosure, there is provided a computer program comprising computer-readable code segments which, when executed by a processor of a computer, causes the computer to perform any of, or any combination of, the method steps described above.

The computer program may be stored in a non-transitory hardware memory device of the computer.

More advantageous aspects of the clinical decision support system and the associated method and computer program will be described in the detailed description of embodiments following hereinafter.

BRIEF DESCRIPTION OF THE DRAWINGS

The invention(s) of the present disclosure will become more fully understood from the detailed description provided hereinafter and the accompanying drawings, which are given by way of illustration only. In the different drawings, same reference numerals correspond to the same element.

DETAILED DESCRIPTION

The present disclosure relates to a clinical decision support system and an associated method and computer program. The clinical decision support system is configured to perform an event correlation trend (ECT) analysis where physiologically linked events are monitored to establish and present a trend of correlation between the events. Thus, the clinical decision support system may as well be characterized as an event monitor for monitoring different types of physiological events and correlation between different types of physiological events.

Figure 1:
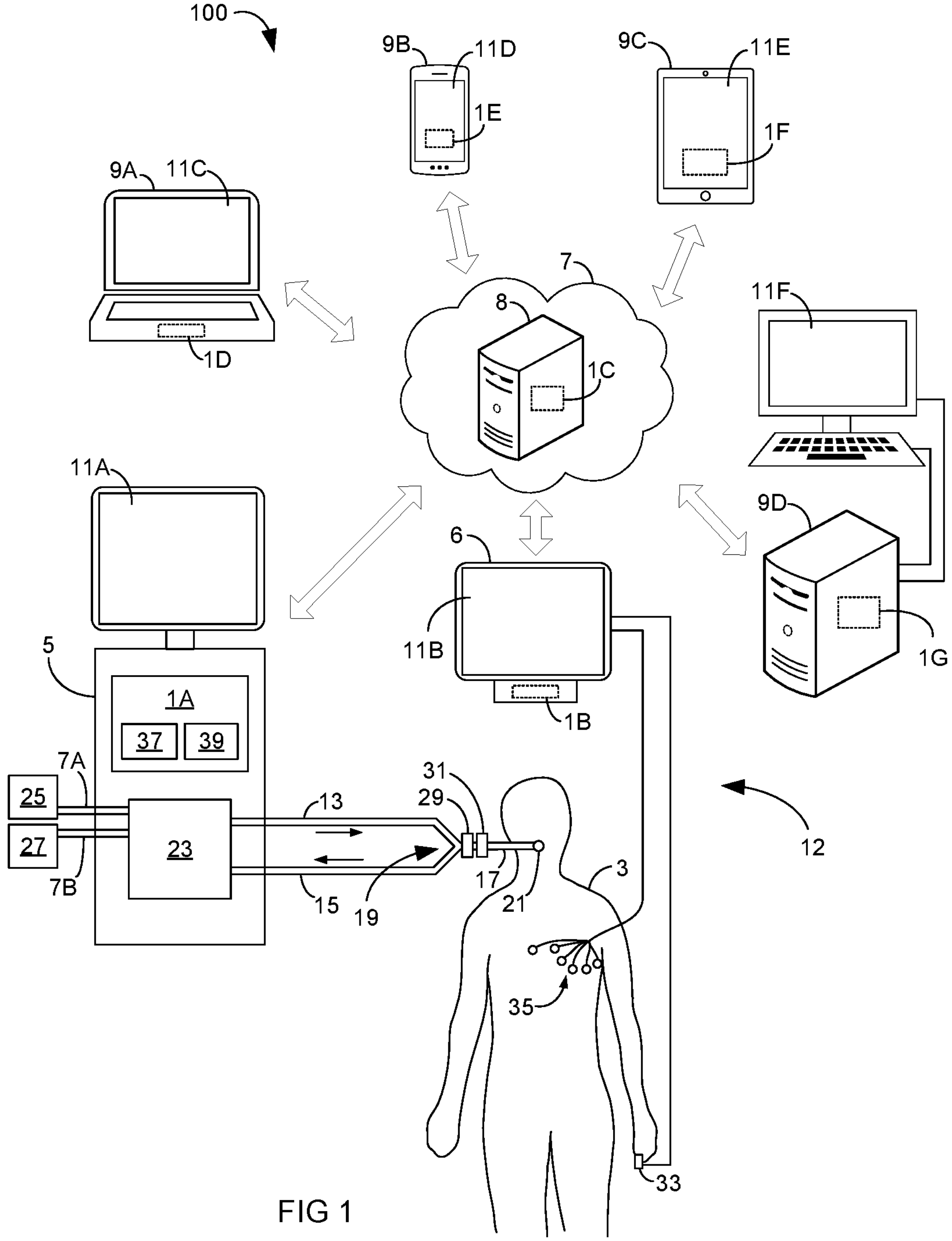
FIG. 1 illustrates a clinical decision support system according to an exemplary embodiment of the present disclosure.

With reference now made to FIG. 1, a clinical decision support system 100 according to an exemplary embodiment of the present disclosure may comprise at least one computer 1A-1G configured to perform the ECT analysis based on physiological parameters obtained during a period of mechanical ventilation of a patient 3.

The physiological parameters are typically obtained by a breathing apparatus 5 (e.g. a ventilator or an anaesthesia apparatus) performing the mechanical ventilation of the patient 3, and/or a patient monitoring system 6 for monitoring physiological parameters of the ventilated patient. The computer performing the ECT analysis may be an internal computer 1A of the breathing apparatus 5, a computer 1B of the patient monitoring system 6, or it may be a computer 1C-1G of a device that is configured to directly or indirectly receive the physiological parameters from the breathing apparatus 5. The computer may for instance be a computer that is connected to the breathing apparatus 5 via a network, such as the Internet, represented by a cloud 7 in the drawing. The computer may be a computer 1C residing in an application server 8 on the network, allowing client computers 1D-1G to connect to the server to take part of the result of the ECT analysis. In this instance, the client computer 1D-1G may be a computer residing in a client device such as laptop 9A, a smart phone 9B, a personal digital assistant (PDA) 9C, or a stationary work station 9D. In other embodiments, the client computer 1D-1G of the client device 9A-9D may be the computer actually performing the ECT analysis based on physiological parameters received either directly from the breathing apparatus 5, the patient monitoring system 6, and/or from the server 8.

The result of the ECT analysis is a visual presentation of event correlation trend data indicative of a trend of correlation between a primary physiological event and at least one secondary physiological event, which events are identified from physiological parameters which, in this exemplary embodiments, are obtained during a period of mechanical ventilation of the patient 3. The event correlation trend data may be presented on a display 11A of the breathing apparatus 5, a display 11B of the patient monitoring system 6, and/or a display 11C-11F of any of the client devices 9A-9D.

The breathing apparatus 5 and the monitoring system 6 form part of a ventilation system 12. The breathing apparatus 5 may be any type of breathing apparatus for providing ventilatory assist to a patient, such as a ventilator, an anaesthesia apparatus, a CPAP machine or a device for providing oxygen flow therapy to the patient 3, e.g., a high-flow oxygen device. In the illustrated embodiment, the breathing apparatus 5 is a mechanical ventilator.

The breathing apparatus 5 is connected to the patient 3 via a patient circuit comprising an inspiratory line 13 for supplying breathing gas to the patient during inspiration, and an expiratory line 15 for conveying expiration gas away from the patient during expiration. The inspiratory line 13 and the expiratory line 15 are connected to a common line 17, via a so called Y-piece 19, which common line is connected to the patient 3 via a patient connector 21, such as a facemask or an endotracheal tube.

The computer 1A of the breathing apparatus 5 may be a control computer for controlling the ventilation of the patient 3 based on pre-set parameters and/or measurements obtained by various sensors of the breathing apparatus. The computer 1A controls the ventilation of the patient 3 by controlling a pneumatic unit 23 of the breathing apparatus 5, which pneumatic unit 23 is connected on one hand to one or more gas sources 25, 27 and on the other hand to the inspiratory line 13 for regulating a flow and/or pressure of breathing gas delivered to the patient 3. The pneumatic unit 23 may comprise various gas mixing and regulating means well known in the art of ventilation, such as gas mixing chambers, controllable gas mixing valves, turbines, controllable inspiration and/or expiration valves, etc. The pneumatic unit 23 is connected to the inspiratory line 1 of the patient circuit via an internal inspiratory flow channel of the breathing apparatus 5, and to the expiratory line 15 of the patient circuit via an internal expiratory flow channel of the breathing apparatus. The gas flow path of the ventilation system 12 that is arranged in fluid communication with the airways of the patient 3 during operation of the breathing apparatus 5 may herein be referred to as the breathing circuit of the ventilation system. The breathing circuit includes at least the patient circuit and the internal inspiratory and expiratory flow channels of the breathing apparatus 5.

The ventilation system 12 comprises one or more sensors for measuring the physiological parameters used to identify the events for which the event correlation analysis is to be performed. The type and number of sensors required for the event correlation analysis depend on what physiological parameters need to be monitored and analysed in order to identify the primary and the at least one secondary physiological events.

In the exemplary embodiment illustrated in FIG. 1, the ventilation system comprises at least one respiratory sensor for obtaining respiratory activity data from the patient 3. In the illustrated embodiment, the at least one respiratory sensor comprises a flow sensor 29 for measuring inspiratory and/or expiratory flow, and a pressure sensor 31 for measuring a proximal pressure substantially corresponding to the airway pressure of the patient 3. Yet further, the ventilation system 12 comprises a blood oxygen sensor 33, such as a pulse oximeter, for measuring oxygen content or concentration in the ventilated patient's blood. The blood oxygen sensor 33 may be attached to a body part of the patient 3, such as a fingertip, an earlobe or a foot, in order to obtain oxygenation data relating to the oxygenation of blood in the body part. The blood oxygenation data may, for instance, comprise data on peripheral oxygen saturation (SpO2). The ventilation system 12 also comprises a heart rate sensor 35 for measuring the heart rate of the ventilated patient 3. The heart rate sensor 35 may be an electrocardiogram (ECG) sensor configured to register ECG signals indicative of the electrical activity of the heart of the patient 3.

In the illustrated embodiment, the heart rate sensor 35 is an ECG sensor comprising a set of surface electrodes for registering the ECG of the patient in a well-known manner. In other embodiments, the heart rate sensor may be a so called Edi catheter inserted into the oesophagus of the patient for picking up myoelectric signals representative of the electrical activity of the patient's diaphragm. An Edi catheter is normally used during neurally adjusted ventilatory assist (NAVA) in order for a NAVA-enabled breathing apparatus to control the delivery of breathing gas in synchrony with and in proportion to the patient's breathing efforts, as indicated by the registered myoelectric signals. However, the signals registered by the Edi catheter normally comprise ECG components, which may be extracted using signal processing to obtain information on the heart rate of the patient.

Thus, in the illustrated embodiment, the ventilation system 12 comprises a flow sensor 29 for measuring inspiratory and/or expiratory flow, a pressure sensor 31 for measuring a proximal pressure, a blood oxygen sensor 33 for measuring SpO2, and a heart rate sensor 35 for measuring the heart rate of the patient 3. In an exemplary embodiment that will be described in greater detail below, the event correlation trend analysis is performed for the physiological events apnea, bradycardia and oxygen desaturation. In this case, inspiratory flow measurements, expiratory flow measurements, and/or proximal pressure measurements may be used to identify apnoeic events, SpO2 measurements may be used to identify oxygen desaturation events, and heart rate measurements may be used to identify bradycardia events.

It should be realised that the specific sensor setup in FIG. 1 is only exemplary, and that the present disclosure is not limited to the use of any particular type of sensor or sensor setup. Nor is the present disclosure limited to the use of any particular physiological parameters for performing the ECT analysis. For example, an Edi catheter may be used not only for detection of bradycardia. The Edi catheter may also be used for detection of apnea, and in particular for detection of central apnea caused by the non-transmission of respiratory signals from the respiratory centre of the brain to the diaphragm of the patient. Yet other examples of respiratory sensors that may be used for the detection of apnea are mechanical, electrical and/or optical sensors for measuring movements of the chest and/or abdominal wall of the patient. Such sensors may for instance be used to detect apnea in clinical situations where the patient's breathing is not monitored by measuring breathing-related bioelectrical signals, respiratory flows or respiratory pressures. In an exemplary alternative embodiment, a respiratory inductive plethysmograph may be used to identify apnoeic events of a patient that is not connected to a breathing apparatus.

As described above, the ECT analysis may be performed by any of the computers 1A-1G in FIG. 1. In the following, only by way of example, the ECT analysis will be described as being performed by the computer 1A of the breathing apparatus 5 through execution of a computer program installed on the breathing apparatus. It should thus be appreciated that any of the computers 1A-1G may be devised and configured in the same way as the computer 1A, and that the computer program for performing the trend correlation analysis may just as well be installed on any of the patient monitoring system 6, the server 8 or the client devices 9A-9D.

The computer 1A of the breathing apparatus 5 comprises a processor 37 and a non-volatile memory 39, typically in form of a non-volatile memory hardware device. Besides one or more computer programs for controlling the ventilation of the patient 3, the memory 39 stores a computer program for supporting a clinician in decisions relating to the mechanical ventilation of the patient 3, i.e., a computer program for clinical decision support. The computer program comprises computer-readable instructions for causing the computer 1A to perform the ECT analysis based on the physiological parameters obtained from the patient 3, according to the principles described herein. The computer program for performing the ECT analysis will hereinafter be referred to as the ECT program.

The ECT program operates to effect a graphical user interface (GUI) so as to allow a user to configure, initiate and evaluate an ECT analysis via different views of the GUI. The GUI is a hardware device that includes a touchscreen display with soft keys or a display and a keyboard, although the ECT program is also a component of the GUI. This user interface will hereinafter be referred to as the ECT tool.

The ECT tool comprises an Event Selection view (not shown) in which the user may select the physiological events for which the ECT analysis is to be performed. The Event Selection view may comprise a list of predefined groups of events for selection by the user, or it may comprise a list of individual events from which the user may select two or more events to be subject to ECT analysis. The ECT tool may also comprise an Event Definition view (not shown) allowing the user to define an event or adjust the definition of a predefined event. An event is typically defined in terms of one or more conditions for one or more measured physiological parameters, or one or more conditions for one or more parameters that are calculated from measured physiological parameters. For example, an apnea event may be defined as an event where measured inspiratory flow is below a set threshold value (typically near zero flow) for more than a predetermined period of time, a bradycardia event may be defined as an event where measured heartrate falls below a set threshold value, and an oxygen desaturation event may be defined as an event where measured SpO2 falls below a set threshold value. The Event Definition view may also allow the user to define new events and to review and adjust the definition of predefined events.

The Event Selection view also allows the user to select one physiological event to be set as primary physiological event during the ECT analysis. The primary physiological event can be said to constitute a main event or base event for the ECT analysis, and the purpose of the ECT analysis is to establish the correlation between the primary physiological event and one or more secondary physiological events, and the change over time (i.e., the trend) of the correlation between the primary physiological event and the one or more secondary physiological events.

The ECT tool may further comprise a Data Selection view allowing the user to select a data set for the ECT analysis, i.e., to select a set of physiological parameters that is to be analysed to identify the events for which the ECT analysis is to be performed. This may generally be regarded as defining a time period of data collection for which the ECT analysis is to be performed. This time period may hereinafter be referred to as the ECT period.

In the Data Selection view, the user may be prompted to input information on whether the ECT analysis is to be performed online, meaning that the ECT analysis is performed based on physiological parameters that are obtained at least partly in real time or near real time, or whether the ECT analysis is to be performed offline, meaning that the ECT analysis is a post-analysis that is performed based on physiological parameters obtained at a previous occasion.

For both online and offline ECT analyses, the user may be prompted in the Data Selection view to define the ECT period by indicating a duration and a start time for the ECT analysis. For example, the user may indicate that the ECT analysis should be an offline ECT analysis of physiological parameters obtained during the last 24 hours. In another example, the user may indicate that the ECT analysis should be an online ECT analysis that is to be based on physiological parameters obtained during the next 5 hours to come.

The ECT tool may further be configured to allow an online ECT analysis to be performed partly retrospectively and partly in real time. For example, the user may select that an online ECT analysis is to be performed for a four hours period, starting two hours ago. The ECT tool may then be configured to perform a partial ECT analysis on physiological parameters already obtained (during the last two hours), and to present the result of the partial ECT analysis to the user. Results of ECT analysis performed on real time data may then be continuously added to the result of the partial ECT analysis in order for the user to monitor the trend of correlation between the physiological events in real time.

When the user has selected a primary physiological event, at least one secondary physiological event and the ECT period for the ECT analysis, the user may initiate the ECT analysis, e.g., by pressing a start button of the ECT tool. The start button may be a soft key of the GUI or it may be a physical button of a keyboard or it may be a physical switch of the breathing apparatus 5.

The trend of correlation between the primary physiological event and the at least one secondary physiological event may be established and presented to a user in many different ways. An exemplary and non-limiting way of doing so will be described in the following with reference to a Trend Evaluation view 40 of the ECT tool, illustrated in FIG. 2.

In this non-limiting example, the user is assumed to have selected apnea as primary physiological event, bradycardia as a first secondary physiological event, and oxygen desaturation as a second secondary physiological event. The user-adjustable definition of an apnea event may, for instance, be set to an inspiratory flow falling below a certain threshold value (e.g., a threshold value slightly above zero flow) during a period of at least 10 s, the user-adjustable definition of a bradycardia event may, for instance, be set to a heart rate (HR) falling below 100 bpm (neonatal bradycardia), and the user-adjustable definition of an oxygen desaturation event may, for instance, be set to SpO2 falling below 86%. It should be noted that bradycardia for adults is generally recognized as a heart rate below 60 beats per minute (bpm). Oxygen desaturation may constitute any oxygen saturation level falling below normal (i.e., below 96% to 98% at sea level). The purpose of permitting a clinician to define bradycardia and oxygen desaturation as a clinical event is so that such events may be defined and customized for a particular patient based on what the clinician deems to be a significant clinical event for that particular patient.

Once the ECT analysis is initiated, the ECT program starts analysing the physiological parameters obtained during the ECT period to identify primary physiological events. In this exemplary embodiment, this means that the ECT program starts analysing the inspiratory flow measurements obtained by the flow sensor 29 in FIG. 1 in order to determine whether the inspiratory flow has fallen below the set threshold value for 10 seconds or more, in which case an apnea event is identified and recorded by the clinical decision support system 100. If a primary physiological event is identified, the ECT program performs a secondary event analysis to determine whether there are any secondary physiological events that are physiologically linked to the identified primary physiological event.

That a secondary physiological event is physiologically linked to a primary physiological event herein means that the secondary physiological event can be assumed to be occasioned by the primary physiological event, or vice versa, or that they can both be assumed to be occasioned by the same physiological event. In other words, primary and secondary physiological events are events that are related because one causes the other and/or they are both related to the same physiological event that causes both the primary and secondary physiological event. When primary and secondary physiological events are so causally related, there will be a discernible correlation between such events.

There are different ways in which the ECT program may perform the secondary event analysis. Typically, the ECT program is configured to analyse whether there is a causal relationship between an identified primary physiological event and any identified secondary physiological events. If there is a predefined causal relationship between the occurrence of the primary physiological event and the occurrence of a secondary physiological event, it can be assumed that there is a physiological link between the two events and the ECT program may classify the secondary physiological event as physiologically linked to the identified primary physiological event.

In an exemplary and straight forward implementation, the ECT program may be configured to, for each identified primary physiological event, define a time slot in relation to the time of occurrence of the primary physiological event, and to classify any secondary physiological event occurring within that time slot as being physiologically linked to the identified primary physiological event. The length of the time slot and the position in time of the time slot in relation to the point in time of occurrence of the primary physiological parameter may be pre-set by the ECT program based on the type of the events, the category of the ventilated patient, etc. Preferably, the length and the position in time of the time slot are adjustable by the user. For example, a time slot for classifying a bradycardia event or an oxygen desaturation event as being physiologically linked to an identified apnea event may start at the time of occurrence of the apnea event and have a length of 20 seconds. It should be noted that a time slot for classification of secondary physiological events as being physiologically linked to an identified primary physiological event may, depending on the types of primary and secondary events, be set to start before, at or after the occurrence of the primary physiological event.

The ECT program may be configured to categorise each identified primary physiological event based on any secondary physiological event that is physiologically linked to the primary physiological event. There may, for instance, be one primary physiological event (PPE) category for primary physiologically events that are not physiologically linked to any secondary physiological event, one PPE category for each type of linked secondary physiological event, and one PPE category for each type of combination of linked secondary physiological events.

For example, in the illustrated embodiment, there are four different PPE categories for apnea (i.e., apnea being the primary physiological event):

category I: Only apnea,
category II: Apnea with bradycardia,
category III: Apnea with oxygen desaturation, and
category IV: Apnea with both bradycardia and oxygen desaturation.

Category I is referred to as "Only apnea" in the Trend Evaluation view 40 and is the category of all apnea events that are not physiologically linked to any bradycardia event or oxygen desaturation event. Category II is referred to as "Bradycardia" in the Trend Evaluation view 40 and is the category of all apnea events that are physiologically linked only to a bradycardia event. Category III is referred to as "Desaturation" in the Trend Evaluation view 40 and is the category of all apnea events that are physiologically linked only to an oxygen desaturation event. Category IV is referred to as "Brady & desat" in the Trend Evaluation view 40 and is the category of all apnea events that are physiologically linked to both a bradycardia event and an oxygen desaturation event.

The Trend Evaluation View 40 comprises an Event Tracking pane 41 for visualising identified events during the ECT period, or during a user-selected part of the ECT period. The Trend Evaluation View 40 with its Event Tracking pane 41 may, for example, be displayed by display 11A of the breathing apparatus 11A, which forms a component of the GUI. However, in accordance with this disclosure, the GUI may employ other displays as components of the GUI, such as one or more of displays 11B, 11C, 11D, 11E and 11F, to display the Trend Evaluation View 40 with its Event Tracking pane 41. In this way, a clinician may choose to use one of a number of different device displays to view the Trend Evaluation View 40 and the Event Tracking pane 41, and/or multiple clinicians may simultaneously access the same information provided by the Trend Evaluation View 40 and the Event Tracking pane 41 via different devices located at different places.

The visualisation of identified events indicates the points in time of identification of primary physiological events, and the category of each identified primary physiological events. The Event Tracking pane 41 may for instance comprise a timeline with indicators indicating primary physiological events, where each indicator has a visual appearance associated with a specific PPE category. In the illustrated example, each indicator is displayed with a colour that is associated with a specific PPE category, as explained to the user by a colour legend 45 of the Event Tracking pane 41. In another embodiment, there may be different symbols for different PPE categories. The timeline of the Event Tracking pane 41 may be scalable by the user in order for the user to zoom in on relevant parts of the ECT period. The user may also indicate a specific event in the Event Tracking pane 41 to get detailed information on the specific event. Such detailed information may, for instance, comprise information on the magnitude of the primary physiological event (e.g., in terms of time of apnea) and the magnitude of any secondary physiological event to which the primary physiological event is linked (e.g., the heartrate during a bradycardia event or the SpO2 during an oxygen desaturation event).

The ECT program is further configured to count the numbers of identified primary physiological events in each PPE category. The numbers of identified primary physiological events in each PPE category as a function of time constitute what is herein referred to as event correlation trend data, which data are indicative of the trend of correlation between the primary physiological event and any secondary physiological event. The ECT program is configured to present the event correlation trend data, via one of the displays of the clinical decision support system 100, to the user in a manner that clearly visualises the trend of correlation between the primary physiological event and any secondary physiological event that is physiologically linked to the primary physiological event. The event correlation trend data may, of course, be presented to the user in different ways.

In the illustrated example, the ECT program is configured to present an event correlation trend plot 47A in a Correlation Trend pane 49 of the Event Evaluation view 40. The correlation trend plot 47A comprises a visualisation of the number of primary physiological events in each PPE category as a function of time.

The ECT program may be configured to divide the ECT period into a number of discrete time windows. The duration of each time window may be predefined or user-selectable. The duration of each time window may also be determined by the ECT program based on the duration of the ECT period, e.g., as a set percentage of the duration of the ECT period. Different time windows may have different durations and the duration of each time window may be weighted based on the distance in time to the time window from a current time. The weighting may be performed such that distant time windows are given shorter durations than more current time windows.

The dividing of the ECT period into discrete time windows enables the number of primary physiological events in each PPE category as a function of time to be determined by the ECT program by calculating the number of events in each PPE category identified within the respective time window. The result of the calculation may be visualised in a data table 51 constituting a Correlation Trend table, as illustrated in FIG. 3. The data table 51 itself is a visualisation of the trend of correlation between the primary physiological event and secondary physiological event and may be presented in the Correlation Trend pane 49, e.g., upon the click of a button 53 labelled "Correlation Trend Table" in the Trend Evaluation view 40 illustrated in FIG. 2. In an embodiment of this disclosure, Correlation Trend Table button 53 is implemented as a soft key on a touch screen of one or more of the displays 11A, 11B, 11C, 11D, 11E, 11F, and when Correlation Trend table button 53 is activated, the data table 51 is displayed within a portion of Correlation Trend pane 49 or is displayed as a window overlaid on the Correlation Trend pane 49.

Figure 2:
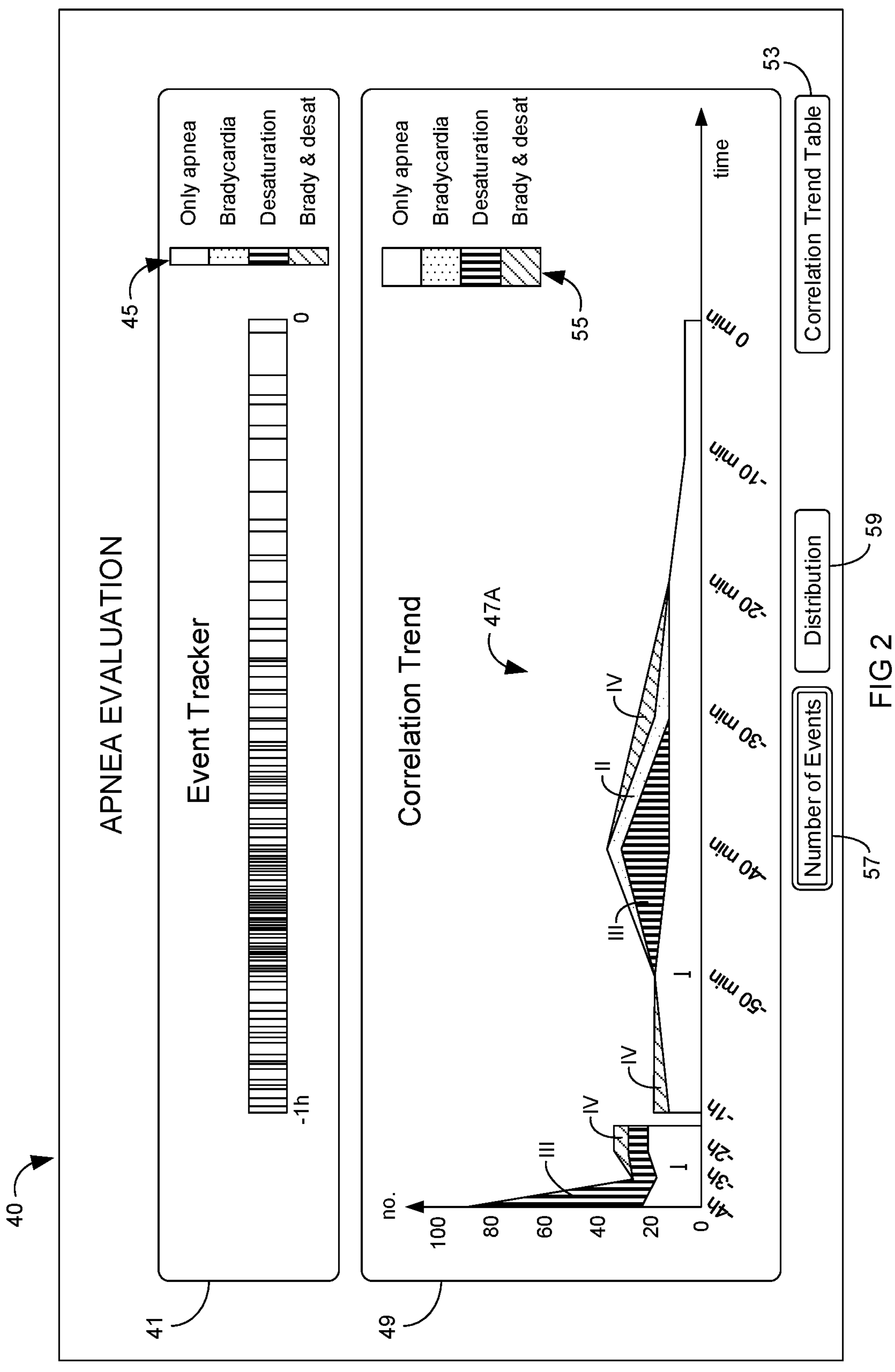
FIG. 2 illustrates an exemplary embodiment of a Correlation Evaluation view of a graphical user interface of a computer of the system that employs a computer program for performing an event correlation trend analysis in accordance with the principles of the present disclosure.
Figures 3, 4:
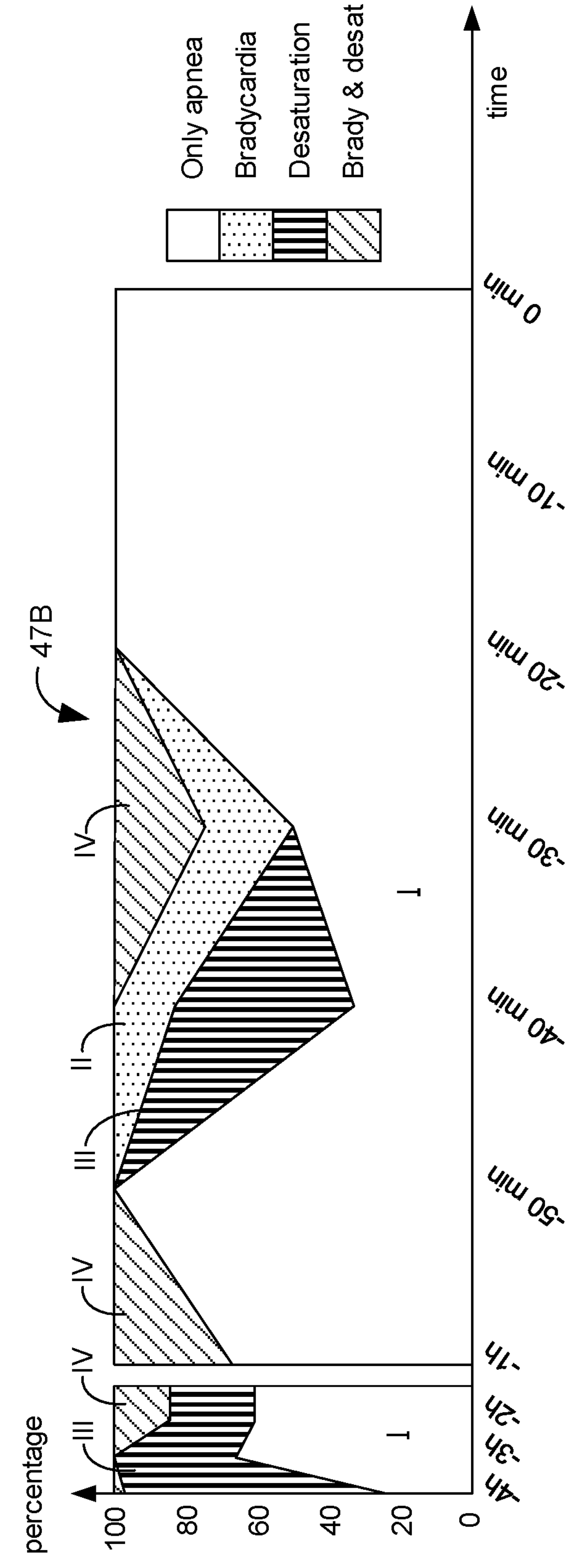
FIG. 3 illustrates a data table comprising event correlation trend data indicative of a trend of correlation between a primary physiological event and secondary physiological events.
FIG. 4 illustrates an event correlation trend plot visualising a distribution of primary physiological events that are physiologically linked to different secondary physiological events, as a function of time.

Preferably, with reference still made to FIG. 2, the event correlation trend plot 47A in the Correlation Trend pane 49 comprises at least one graph illustrating the trend of correlation between the primary physiological event and the at least one secondary physiological event. When there are two or more secondary physiological events, the event correlation trend plot 47A may comprise multiple graphs, where each graph illustrates a trend of correlation between the primary physiological event and a respective secondary physiological event. The event correlation trend plot 47A further comprise one or more graphs illustrating a trend of correlation between the primary physiological event and combinations of secondary physiological events. Yet further, the event correlation trend plot 47A may comprise a graph illustrating a trend for primary physiological events not being linked to any secondary physiological event at all.

In the illustrated embodiment, the ECT program is configured to present an event correlation trend plot 47A comprising one graph for each PPE category. Each graph represents the number of primary physiological events of that PPE category for different time windows of the ECT period. The area under each graph has been provided with a reference sign (I, II, III, IV) corresponding to the PPE category represented by the graph. By presenting graphs for different PPE categories in the same plot, an intuitive and easily comprehensible visualisation of the trend of correlation between the primary physiological event and secondary physiological events are provided.

To further facilitate interpretation of the event correlation trend plot 47A, the areas under each graph may be provided with a respective and distinct visual appearance, such as a respective colour or pattern. A legend 55 for assisting the user in identification of the different graphs of the plot may also be presented in the Correlation Trend pane 49. For the sake of brevity, the patterns shown in the four PPE categories of FIG. 2 of the legends 45, 55 should be construed as representing different colours. The effect of incorporating all graphs in a common plot (i.e., a colour or pattern coded multi-graph) and providing the areas under each graph with a respective visual appearance is that the relation between different areas becomes visually easily comprehensible by the user. The sizes, shapes and relative positions of the areas give the user an immediate understanding of the trend of correlation between the primary physiological event and the secondary physiological events, and thus a deeper understanding of developments in the physiological state of the ventilated patient 3.

An effect of the above mentioned weighting of the duration of time windows is that the resolution of the ECT analysis can be made lower for distant time periods than for more recent time periods. In combination with the use of a nonlinear timescale for the event correlation trend plot 47A, trends of correlation between more recent physiological events may be more clearly visualised (the areas under the graphs become bigger for more recent events) while still offering a clear and visually perspicuous overview of more long-term trends. In the illustrated embodiment of FIG. 2, the duration of time windows for the last hour of ventilation has been set to 10 minutes, whereas the duration of more distant time windows has been set to 1 hour. The nonlinearity of the timescale of the event correlation trend plot 47A may thus be set based on the various durations of the time windows, so as to obtain an easily comprehensible visualisation of the event correlation trends over the entire period of ventilation.

FIG. 4 illustrates an alternative event correlation trend plot 47B indicative of the trend of correlation between the primary physiological event and secondary physiological events, which event correlation trend plot 47B may be presented in the Correlation Trend pane 49 instead of, or in addition to, the event correlation trend plot 47A. The graphs and the associated areas I-IV in the plot 47B corresponds to the graphs and associated areas I-IV in the event correlation trend plot 47A described above. The difference between the plots 47A and 47B is that the graphs I-IV in plot 47A illustrate the number of primary physiological events in each PPE category as a function of time, whereas the graphs I-IV in plot 47B illustrate the distribution of primary physiological events between the PPE categories as a function of time. This is because the vertical axis in plot 47A represents the number of events whereas the vertical axis in plot 47B represents the percentage of events with respect to the total number of events. In plots 47A and 47B, the horizontal axis pertains to time.

This is advantageous in that the distribution graphs in plot 47B provide an even more easily comprehensible visualisation of the trend of correlation between the primary physiological event and the secondary physiological events. The Event Evaluation view 40 of the ECT tool may comprise one or more buttons (i.e., soft keys of a touchscreen or electromechanical keys of a keyboard) enabling the user to toggle between "numeric view" and "distributional view" by presenting any of the event correlation trend plots 47A or 47B to the user in response to user manipulation of the one or more buttons. In the example illustrated in FIG. 2, the Event Evaluation view comprises a first button 57 for numeric view, labelled "Number of Events", and a second button 59 for distributional view, labelled "Distribution". In response to a click on the distribution button 59, the ECT program replaces the event correlation trend plot 47A in the Correlation Trend pane 49 with the event correlation trend plot 47B illustrated in FIG. 4.

Figure 5:
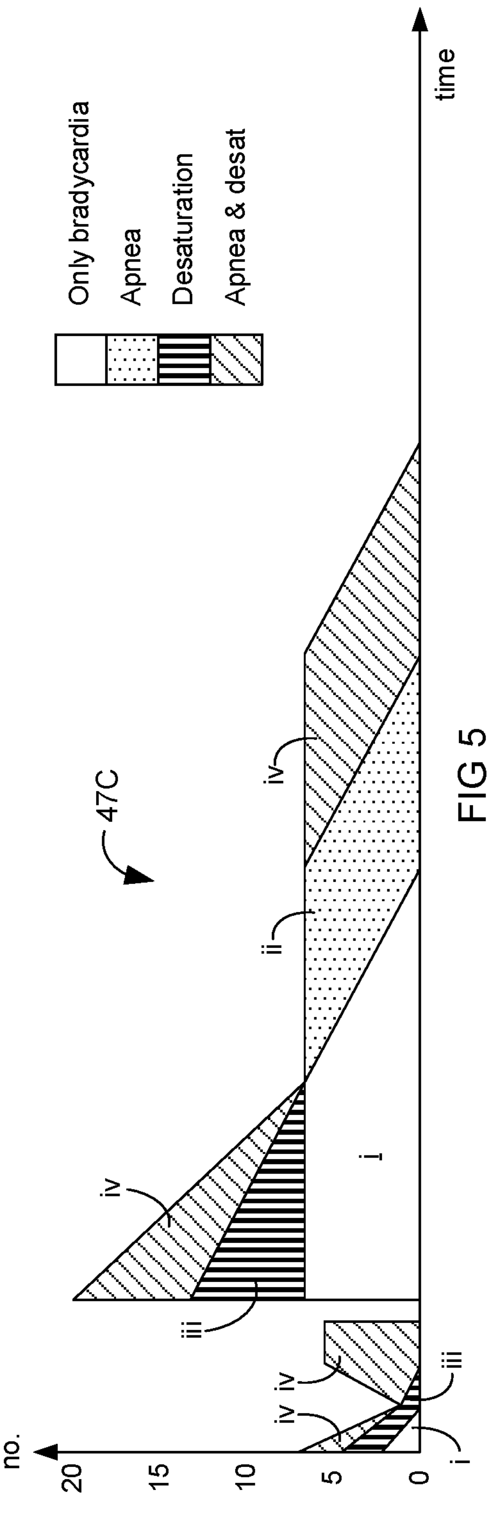
FIG. 5 illustrates an event correlation trend plot visualising number of primary physiological events that are physiologically linked to different secondary physiological events, as a function of time.
Figure 6:
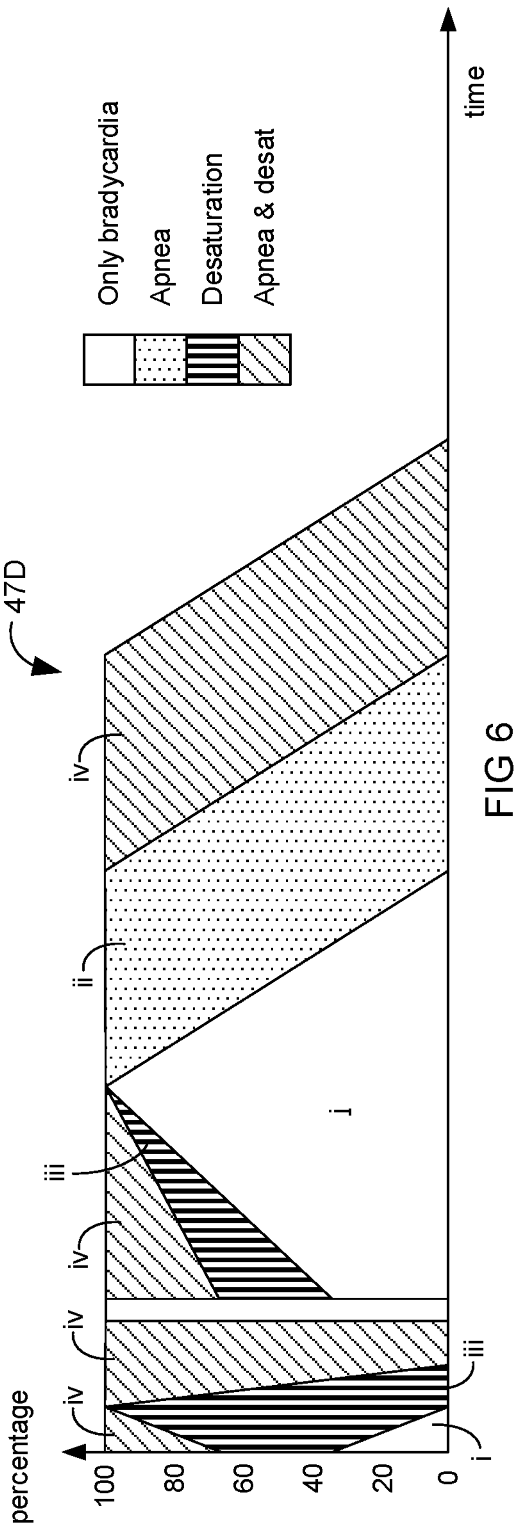
FIG. 6 illustrates another example of an event correlation trend plot visualising a distribution of primary physiological events that are physiologically linked to different secondary physiological events, as a function of time.
Figure 7:
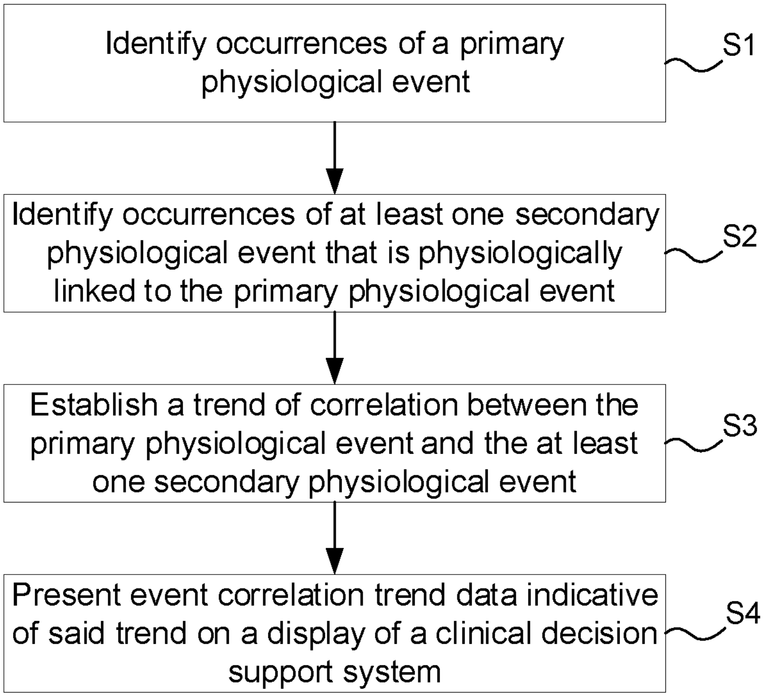
FIG. 7 is a flowchart illustrating a method for clinical decision support, according to an exemplary embodiment of the present disclosure.

For the sake of illustration, FIGS. 5-6 show event correlation trend plots 47C, 47D for a different primary physiological parameter and another set of PPE categories. In this example, bradycardia is selected primary physiological event, whereas apnea and oxygen desaturation is selected secondary physiological events. In analogy with the example described above with reference to FIGS. 2-4, the ECT program may be configured to categorise all identified bradycardia events into any of the following PPE categories:

category i: Only bradycardia,
category ii: Bradycardia with apnea,
category iii: Bradycardia with oxygen desaturation, and
category iv: Bradycardia with both apnea and oxygen desaturation.

The event correlation trend plot 47C in FIG. 5 is a numeric plot illustrating the number of bradycardia events of each PPE category (vertical axis) as a function of time (horizontal axis), whereas the event correlation trend plot 47D in FIG. 6 is a distributional plot illustrating the distribution (percentages) of bradycardia events of different PPE categories (vertical axis) as a function of time (horizontal axis). The ECT program may allow the user to change the selection of primary physiological event and the selection of the one or more secondary physiological events in order for the user to have ECT analyses performed for different primary physiological events based on the same data set.

The event correlation trend plot 47A-47D provided by the ECT tool gives the user, e.g., a breathing apparatus operator (respiratory therapist, physician or nurse) or other medical personnel having a clinical responsibility of the ventilated patient, a useful tool in the assessment of the physiological state of the ventilated patient 3. For instance, in the case of an event correlation trend plot illustrating the trend of correlation between apnea and bradycardia, and between the apnea and oxygen desaturation, the event correlation trend plot gives the user easily comprehensible feedback on any progress of the physiological state of the patient. A positive trend in the meaning of decreased correlation between apnea and bradycardia and between apnea and oxygen desaturation indicates to the user that the physiological state of the patient is improving and that the patient may be ready for and subject to weaning from mechanical ventilation. Likewise, in scenarios where the ECT program is used to monitor a patient undergoing CPAP therapy or oxygen flow therapy, decreased correlation between apnea and bradycardia and/or oxygen desaturation indicates that the ongoing respiratory therapy may be decreased or interrupted. The ECT program may also be used to verify that respiratory treatment of a subject is not required. For instance, a patient that is not subject to respiratory treatment may be monitored by a clinical monitoring system running the ECT program, whereby a decreased or non-existing correlation between apnea and bradycardia and/or oxygen desaturation may indicate that the subject does not require respiratory treatment.

In this regard it should be noted that the ECT program may further be configured to provide the user with recommendations relating to the mechanical ventilation of the patient 3, based on the result of the ECT analysis. For example, in the illustrated embodiment, the ECT program may be configured to cause the display of a recommendation relating to the mechanical ventilation of the patient 3 on a display 11A-11F of the clinical decision support system 100 in response to the result of the ECT analysis. For instance, the ECT program may be configured to cause the display of a dialogue window on the display of the clinical decision support system, asking the user to consider weaning the patient from mechanical ventilation, based on the result of the ECT analysis. An exemplary embodiment in which the ECT program is configured to present recommendations relating to mechanical ventilation of a patient based on the result of the ECT analysis will be further described below with reference to FIG. 9.

In embodiments where the ECT program is not used for a mechanically ventilated patient but for a patient that is subject to another medical treatment, e.g., another respiratory treatment, such as CPAP therapy or oxygen flow therapy, other treatment-specific recommendations may be displayed to the clinician based on the result of the ECT analysis. For example, when the ECT program is used in the monitoring of a patient undergoing CPAP therapy or oxygen flow therapy, the ECT program may recommend that the therapy is decreased or interrupted (weaning from CPAP or oxygen flow therapy) if the ECT analysis indicates a non-existing or decreasing correlation between, e.g., apnea and bradycardia, and/or between apnea and oxygen desaturation. If, on the other hand, the ECT analysis indicates an existing or increasing correlation between, e.g., apnea and bradycardia, and/or between apnea and oxygen desaturation, the ECT program may recommend that the ventilatory support provided to the patient is increased, i.e., that the respiratory treatment is intensified. The ECT program may also be configured to present recommendations on suitable treatments not currently provided to the patient based on the result of the ECT analysis. For example, when the ECT program is used to monitor a patient who is not currently subject to any respiratory treatment, the ECT program may be configured to recommend provision of respiratory treatment, e.g., in the form of mechanical ventilation therapy, CPAP therapy or oxygen flow therapy, to the patient if the ECT analysis indicates an existing or increasing correlation between, e.g., apnea and bradycardia, and/or between apnea and oxygen desaturation.

It should thus be appreciated that the ECT program may be configured to monitor a patient who may or may not be subject to an ongoing respiratory treatment, e.g., in the form of mechanical ventilation therapy, CPAP therapy or oxygen flow therapy. The ECT program may be configured to present a recommendation relating to the ongoing respiratory treatment or a recommendation relating to a recommended but not yet ongoing respiratory treatment of the patient, based on the result of the ECT analysis, i.e., based on the established trend of correlation between the primary physiological event and the at least one secondary physiological event. The recommendation may comprise any of: a recommendation to provide respiratory treatment to the patient or to intensify an ongoing respiratory treatment of the patient; a recommendation to continue monitoring the patient; and, a recommendation to stop monitoring the patient. For example, the ECT program may be configured to recommend that the monitoring of the patient is interrupted if there is no increase in correlation between, e.g., apnea and bradycardia, and/or between apnea and oxygen desaturation correlation, during a period of about 5-7 days.

FIG. 6 is a flowchart illustrating a method for supporting a clinician in decisions relating to a patient, according to an exemplary embodiment of the present disclosure. The method is typically a computer-implemented method performed through the execution of the ECT program by a processor of a computer of a clinical decision support system, such as any of the computers 1A-1G of the clinical decision support system 100 in FIG. 1. For example, the method may be performed by the computer 1A of the breathing apparatus 5 through execution by the processor 37 of the ECT program stored in the memory 39. The method comprises a step of performing an event correlation trend analysis based on physiological parameters obtained from a patient, such as the patient 3 receiving mechanical ventilation form the breathing apparatus 5.

In a first step, S1, of the correlation trend analysis, occurrences of a primary physiological event are identified.

In a second step, S2, occurrences of at least one secondary physiological event that is physiologically linked to the primary physiological event are identified.

In a third step, S3, a trend of correlation between the primary physiological event and the at least one secondary physiological event is established.

In fourth and final step, S4, event correlation trend data indicative of the trend of correlation is displayed on a display of a clinical decision support system. In an embodiment of this disclosure, the event correlation trend data is displayed as a plot comprising multiple graphs of different colours or patterns in order to facilitate a clinician's comprehension of event correlation. The event correlation trend data is displayed on one or more of the displays (e.g., touchscreens) 11A to 11F, Optionally, the method may include one or more additional steps in which the ECT program displays recommended ventilator settings in a dialogue window on at least one of these displays, such as display 11A of the breathing apparatus 5, with or without an actuation button (e.g., soft key on the touchscreen or electromechanical key of a keyboard) for accepting the ventilator settings, and with or without setting modification buttons (e.g., soft keys on the touchscreen or electromechanical keys of the keyboard) to modify the recommended ventilator settings before acceptance by actuating the actuation button. Upon actuation of the actuation button, the ECT program implements the new ventilator settings by controlling the breathing apparatus 5 in accordance with the new ventilator settings.

Consequently, as outlined above, according to one aspect of the present disclosure, there is provided a method for supporting a clinician in decisions relating to a patient. The method comprises a step of performing an event correlation trend analysis based on physiological parameters obtained from the patient, wherein the correlation trend analysis is performed by:

(a) identifying occurrences of a primary physiological event;

(b) identifying occurrences of at least one secondary physiological event that is physiologically linked to the primary physiological event;

(c) establishing a trend of a correlation between the primary physiological event and the at least one secondary physiological event, and (d) presenting event correlation trend data indicative of the trend on a display of a clinical decision support system.

Although the proposed ECT analysis has been described in the context of apnea events, bradycardia events and oxygen desaturation events, it should be appreciated that the teachings of the present disclosure are not limited to any particular types of physiological events. In different clinical situations, the trend of correlation between physiological events other than apnea, bradycardia and oxygen desaturation may be an important input parameter in the assessment of the physiological state of a patient.

Figure 8:
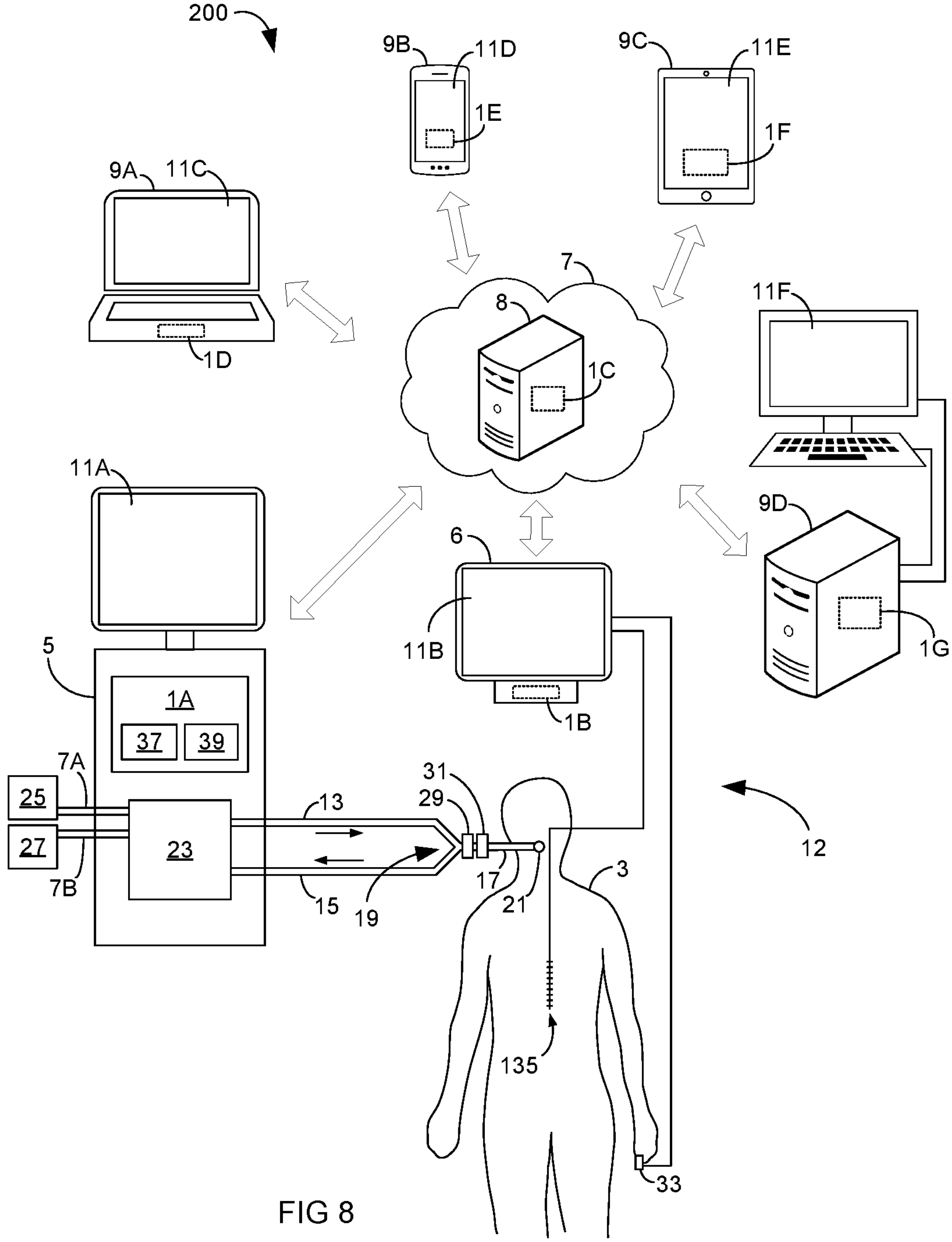
FIG. 8 illustrates a clinical monitoring system according to an exemplary embodiment of the present disclosure.

FIG. 8 illustrates another embodiment of this disclosure pertaining to a clinical monitoring system 200 that is configured to monitor multiple different types of physiological events and to determine correlation between these different types of physiological events, which may be used to improve clinical decision making. The system 200 is provided with at least one computer 1A-1G configured to perform an event correlation trend analysis based on physiological parameters obtained from a patient 3. The system 200 also includes sensors for obtaining physiological parameters that may be used to identify a physiological event. For example, the system 200 may include a heart rate sensor, such as Edi catheter 135 or a pulse oximeter that obtains heart rate data from the patient and that is operably connected to send the heart rate data to the at least one computer 1A-1G, and a blood oxygen sensor 33, such as pulse oximeter, that obtains blood oxygen saturation data from the patient and that is operably connected to send the blood oxygen saturation data to the at least one computer 1A-1G, and a respiratory sensor, such as flow sensor 29, a pressure sensor 31 or the Edi catheter 135, which obtains respiratory activity data from the patient and that is operably connected to send the respiratory activity data to the at least one computer 1A-1G. The system 200 is also provided with a display 11B operably connected to the at least one computer 1A-1G, wherein the display may be a monitor touchscreen and constitute a graphical user interface. The at least one computer may optionally cause data images, graphs and plots to be displayed on other displays 11A, 11C, 11D, 11E, 11F of the system 200. The at least one computer 1A-1G is configured to perform event correlation analysis by identifying and monitoring occurrences of a primary physiological event, wherein identification of occurrences of the primary physiological event is based on one of the heart rate data, the blood oxygen data and the respiratory activity data; identifying and monitoring occurrences of at least one secondary physiological event that is physiologically linked to the primary physiological event, wherein identification of occurrences of the at least one secondary physiological event is based on one of the other two of the heart rate data, the blood oxygen data, and the respiratory activity data; establishing a trend of correlation between the primary physiological event and the at least one secondary physiological event, and presenting event correlation trend data indicative of trends on the display 11B of the clinical monitoring system.

The at least one computer 1A-1G of system 200 may be configured to identify several different types of secondary physiological events, and to establish and present a trend of correlation between the primary physiological event and each of the secondary physiological event types. The computer 1A-1G may be further configured to categorise identified primary physiological events based on the types of physiologically linked secondary physiological events, and to establish the correlation trend by determining the number of primary physiological events of each category as a function of time. Furthermore, the computer 1A-1G may be configured to determine the number of primary physiological events in each category for each of a plurality of discrete time windows.

The computer 1A-1G of system 200 may be configured to present the event correlation trend data in the form of an event correlation trend plot 47A-47D, as shown in FIGS. 2, 4, 5 and 6, which is displayed in a correlation trend pane 49 on the primary monitor display 11B, although the event correlation trend plot may be displayed as well on any of the other displays of the system 200, wherein the event correlation trend plot 47A-47D includes at least one graph illustrating the trend of correlation between the primary physiological event and the at least one secondary physiological event, and occurrences of the primary physiological event and occurrences of the at least one secondary physiological event are displayed in an event tracking pane 41 on the display 11B. In accordance with an embodiment, the event correlation trend plot 47A-47D comprises multiple graphs of different colours or patterns, at least some of which illustrate a trend of correlation between the primary physiological event and a respective type of secondary physiological event as evident from FIG. 2.

The computer 1A-1G of system 200 is configured to categorise identified primary physiological events based on the types of physiologically linked secondary physiological events, and to establish correlation trend by determining the number of primary physiological events of each category as a function of time, and the computer 1A-1G is configured to present the event correlation trend data in the form of an event correlation trend plot 47A-47D displayed in a correlation trend pane 49 on the display 11B, as shown in FIG. 2. In an embodiment, the event correlation trend plot comprises at least one graph illustrating the trend of correlation between the primary physiological event and the at least one secondary physiological event, wherein the multiple graphs are distribution graphs representing the distribution of different categories of primary physiological events as a function of time, and occurrences of the primary physiological event and occurrences of the at least one secondary physiological event are displayed in an event tracking pane 41 on the display 11B. In an embodiment, the event tracking pane 41 and the correlation trend pane 49 are disposed together within a selectable trend evaluation view 40 that is viewable on the display as evident from FIG. 2.

In an embodiment of system 200, the trend evaluation view 40 includes a first button 57 and a second button 59, wherein activation of the first button effects display of the event correlation trend plot as a numeric view whereas activation of the second button effects display of the event correlation trend plot as a distribution view. In this context, buttons 57, 59 and 53, which are displayed on display 11B are soft keys of the graphical user interface operating as part of the touch screen.

In an embodiment of system 200, the primary physiological event is apnea and one or more secondary physiological events are tracked from the group consisting of bradycardia and oxygen desaturation. In an embodiment of system 200, the primary physiological event is bradycardia and one or more secondary physiological events are tracked from the group consisting of apnea and oxygen desaturation.

In an embodiment of system 200, the physiological parameters are obtained during a period of mechanical ventilation of the patient. In an embodiment of system 200, the physiological parameters are obtained during a period of continuous positive airway pressure CPAP therapy administered to the patient. In an embodiment of system 200, the physiological parameters are obtained during a period of oxygen flow therapy administered to the patient, e.g., during a period of supplemental oxygen provision or high-flow oxygen therapy. In an embodiment of system 200, the physiological parameters are obtained during a period of non-provision of respiratory treatment of the patient 3.

The configuration of system 200 is flexible in that the respiratory sensor may be a flow sensor, a pressure sensor or an Edi catheter, or some or all of a flow sensor, a pressure sensor and an Edi catheter may be used in combination. The heart rate sensor may be an ECG sensor, an Edi catheter, or a pulse oximeter, or any combination of these heart rate measuring devices. The blood oxygen sensor may be a pulse oximeter that also serves as the heart rate sensor. Any combination of these or other sensors may be connected to provide physiologic data to the computer 1A-1G, which provides substantial flexibility with respect to selection of sensor configurations.

Figure 9:
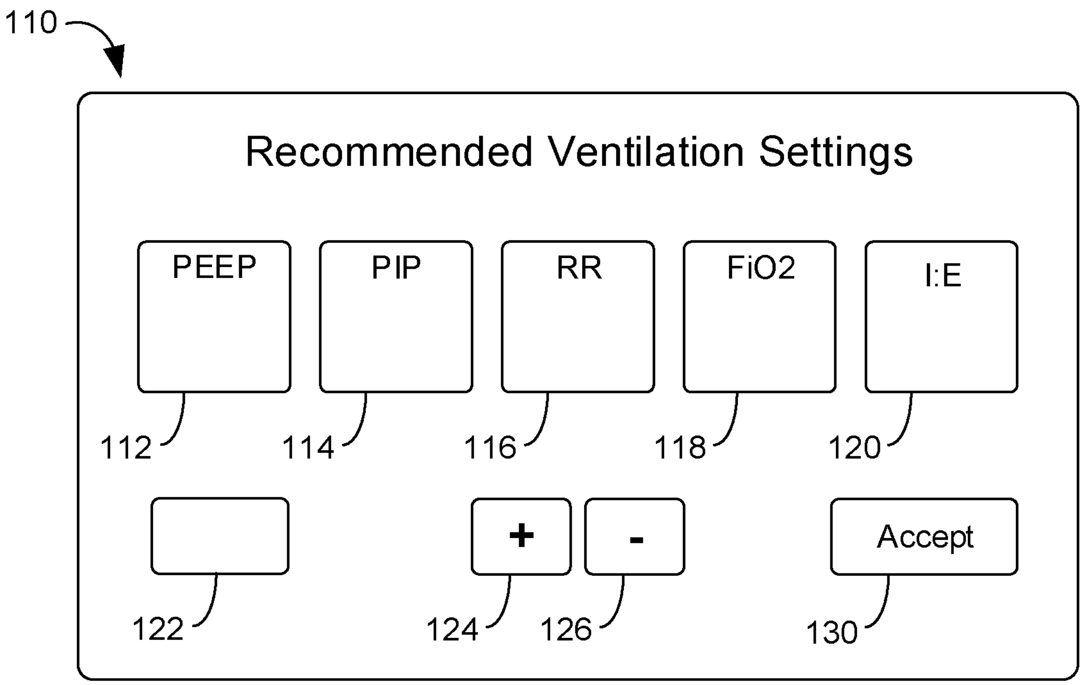
FIG. 9 illustrates a ventilation recommendation pane according to an exemplary embodiment of the present disclosure that may display ventilation recommendations as part of a clinical decision support system, which clinical decision support system may, e.g., form part of a clinical monitoring system or a breathing apparatus.

In an embodiment of system 200, the computer 1A-1G may be configured to present a recommendation related to a treatment of the monitored patient 3 based on the established trend of correlation between the primary physiological event and the at least one secondary physiological event. The recommendation may comprise a recommendation relating to an ongoing treatment of the patient 3, or it may comprise a recommendation relating to recommended but not yet ongoing treatment of the patient 3. The computer 1A-1G may be configured to present the recommendation by displaying it on a recommendation pane 110, as shown in FIG. 9. In the illustrated example in which the patient is mechanically ventilated by the breathing apparatus 5, the recommendation comprises recommended ventilator settings which are presented via recommended ventilator setting panes 112, 114, 116, 118, 120 on the recommendation pane 110. The recommended ventilator settings may, for example, pertain to recommended ventilator settings for positive end expiratory pressure (PEEP), peak inspiratory pressure (PIP), respiratory rate (RR), inspiratory oxygen concentration (FiO2), and inspiratory to expiratory (I:E) ratio, respectively. When there is a significant positive correlation between apnea (primary physiologic event) and either bradycardia and/or oxygen desaturation (secondary physiologic events), the computer 1A-1G provides recommendations with respect to increasing ventilatory support. When there is no significant positive correlation between apnea and either bradycardia and/or oxygen desaturation, then the computer provides recommendations with respect to decreasing respiratory support (i.e., weaning respiratory support). Because computer 1A-1G may more rapidly and efficiently identify such correlations between these physiologic events, computer 1A-1G may provide more efficient recommendations pertaining to management of respiratory support.

In the illustrated example, the recommendation pane 110 is provided with a setting pane selection button 122 which allows a user to scroll through the ventilator setting panes 112, 114, 116, 118, 120 and select one of the panes if a clinician desires to manually modify a recommended ventilator setting of one of the recommended ventilator setting panes using ventilation recommendation modification buttons 124, 126. For example, if a patient is experiencing a significant positive correlation between apnea and bradycardia and/or oxygen desaturation, so the computer recommends increasing respiratory support by increasing respiratory rate setting of setting pane 116 and increasing inspired oxygen concentration of setting pane 118, and the clinician decides the suggested increase in respiratory rate is too much or not enough, the clinician may use ventilation recommendation modification buttons 124, 126 to either increase the recommended respiratory rate increase or decrease the respiratory rate increase, respectively, after setting pane 116 has been selected using button 122. Similarly, ventilation recommendation modification buttons 124, 126 may be used to modify recommended ventilator settings of any of the ventilator setting panes 112, 114, 116, 118, 120 after it has been selected for modification using setting pane selection button 122.

If a clinician desires to accept the recommended ventilator settings presented by the computer via the ventilator setting panes 112, 114, 116, 118, 120, the clinician activates the actuation button 130, and the computer sends control signals to the breathing apparatus 5 so as to operate the breathing apparatus 5 in accordance with the accepted settings. Of course, as described above, the clinician may modify one or more of the recommended ventilator settings prior to accepting the modified recommended ventilator settings by subsequently activating the actuation button 130 after the desired ventilator setting modifications have been made.

Thus, the recommendation pane 110 constitutes a graphical user interface on the touch screen of the display 11B, which includes the actuation button 130 and the ventilation recommendation modification buttons 124, 126, which may be used to modify recommended ventilator settings presented in setting panes 112, 114, 116, 118, 120, wherein the ventilation recommendation modification buttons are actuatable to modify the ventilation recommendations, and the actuation button, when actuated, results in the at least one computer operating the breathing apparatus 5 so as to ventilate the patient in accordance with the ventilation recommendation unless modified by the one or more ventilation recommendation buttons first, in which case the actuation button, when actuated, results in the at least one computer operating the breathing apparatus in accordance with the modified ventilation recommendation. While the embodiment of FIG. 9 is illustrated with two ventilation recommendation modification buttons, in accordance with an embodiment, a single toggle-type button is used instead of the two buttons 124, 126 to provide the same functions of increasing or decreasing a setting value.

In other embodiments where the clinical monitoring system 200 is used not to monitor a mechanically ventilated patient but a patient that is subject to another medical treatment, e.g., another respiratory treatment, such as CPAP therapy or oxygen flow therapy, other treatment-specific recommendations may be displayed to the clinician on the recommendation pane 110, based on the established trend of correlation between the primary physiological event and the at least one secondary physiological event. For example, when the clinical monitoring system 200 is used in the monitoring of a patient undergoing CPAP therapy or oxygen flow therapy, the computer 1A-1G may be configured to present a recommendation to decrease or interrupt the therapy (weaning from CPAP or oxygen flow therapy) if the established trend of correlation indicates a non-existing or decreasing correlation between, e.g., apnea and bradycardia, and/or between apnea and oxygen desaturation. If, on the other hand, the established trend of correlation indicates an existing or increasing correlation between, e.g., apnea and bradycardia, and/or between apnea and oxygen desaturation, the computer 1A-1G may recommend that the ventilatory support provided to the patient should be increased, i.e., that the respiratory treatment should be intensified. The computer 1A-1G may also be configured to present recommendations on suitable treatments not currently provided to the patient based on the established trend of correlation between the primary physiological event and the at least one secondary physiological event. For example, when the clinical monitoring system 200 is used to monitor a patient who is not currently subject to any respiratory treatment, the computer 1A-1G may be configured to recommend provision of respiratory treatment, e.g., in the form of mechanical ventilation therapy, CPAP therapy or oxygen flow therapy, to the patient if the established trend of correlation indicates an existing or increasing correlation between, e.g., apnea and bradycardia, and/or between apnea and oxygen desaturation.

It should thus be appreciated that the clinical monitoring system 200 may be configured to monitor a patient who may or may not be subject to an ongoing respiratory treatment, e.g., in the form of mechanical ventilation therapy, CPAP therapy or oxygen flow therapy. The at least one computer 1A-1G of the clinical monitoring system 200 may be configured to present a recommendation relating to the ongoing respiratory treatment or a recommendation relating to a recommended but not yet ongoing respiratory treatment of the patient, based on the established trend of correlation between the primary physiological event and the at least one secondary physiological event. The recommendation may comprise any of: a recommendation to provide respiratory treatment to the patient or to intensify an ongoing respiratory treatment of the patient; a recommendation to continue monitoring the patient; and, a recommendation to stop monitoring the patient. For example, the computer 1A-1G may be configured to recommend that the monitoring of the patient is interrupted if there is no increase in correlation between, e.g., apnea and bradycardia, and/or between apnea and oxygen desaturation correlation, during a period of about 5-7 days.

The system 200, which is a monitor, monitors the physiologic parameters and records data pertaining to the physiologic parameters in a hardware memory device 1B, and the system 200 monitors identified primary physiological events and identified secondary physiological events and stores data pertaining to the identified primary physiological events and the identified secondary physiological events in the hardware memory device 1B.

The invention claimed is:

1. A method for supporting a clinician in decisions relating to a patient, comprising the steps of:

performing, via a processor, an event correlation trend analysis based on physiological parameters obtained from the patient, the event correlation trend analysis being performed by a clinical decision support system that performs the steps of:

identifying occurrences of a primary physiological event based on a first physiological parameter measured via a first sensor;

identifying occurrences of at least one secondary physiological event that is physiologically linked to the primary physiological event based on at least one second physiological parameter measured via at least one second sensor;

establishing a trend of correlation between the primary physiological event and each of the at least one secondary physiological event during an analysis time period that is divided into discrete time windows, the trend of correlation determined based on event correlation trend data including a number of occurrences of the primary physiological event and each of the at least one secondary physiological events during each of the discrete time windows, wherein the primary physiological event and the at least one secondary physiological event are selected from the group consisting of apnea, bradycardia and oxygen desaturation;

presenting the trend of correlation on a display of the clinical decision support system in real-time via an event correlation trend plot including at least one graph illustrating the trend of correlation between the primary physiological event and the at least one secondary physiological event; and one of increasing and initiating a ventilatory support provided to the patient when a positive trend of correlation is established, wherein the ventilatory support includes one of mechanical ventilation, CPAP and oxygen flow therapy.

2. The method of claim 1, further comprising the steps of:

identifying several different types of secondary physiological events; and establishing and presenting a trend of correlation between the primary physiological event and each of the secondary physiological event types.

3. The method of claim 2, further comprising the steps of:

categorizing identified primary physiological events based on the different types of physiologically linked secondary physiological events; and establishing the trend of correlation by determining a number of primary physiological events of each category as a function of time.

4. The method of claim 3, wherein the number of primary physiological events of each category is determined for each of a plurality of discrete time windows.

5. The method of claim 1, wherein the event correlation trend plot comprises multiple graphs, each illustrating the trend of correlation between the primary physiological event and a respective type of secondary physiological event.

6. The method of claim 5, further comprising the steps of:

categorizing identified primary physiological events based on the types of physiologically linked secondary physiological events; and establishing the trend of correlation by determining a number of primary physiological events of each category as a function of time, wherein the multiple graphs are distribution graphs representing the distribution of different categories of primary physiological events as a function of time.

7. The method of claim 1, wherein the physiological parameters are obtained during a period of mechanical ventilation of the patient.

8. A computer program stored on a non-transitory computer readable medium, the computer program comprising computer-readable code segments which, when executed by a processor of a computer, causes the computer to perform the method of claim 1.

9. A clinical monitoring system configured to monitor multiple different types of physiological events and to determine a correlation between different types of physiological events, the system comprising:

at least one computer configured to perform an event correlation trend analysis based on physiological parameters obtained from a patient;

a first sensor and at least one second sensor, each of the first sensor and the at least one second sensor selected from a group consisting of:

a heart rate sensor obtaining heart rate data from the patient and that is operably connected to send the heart rate data to the computer;

a blood oxygen sensor obtaining blood oxygen saturation data from the patient and that is operably connected to send the blood oxygen saturation data to the computer;

a respiratory sensor obtaining respiratory activity data from the patient and that is operably connected to send the respiratory activity data to the computer; and a display operably connected to the computer, wherein the first sensor and the at least one second sensor are operably connected to the computer, and the computer is configured to perform the event correlation analysis by identifying and monitoring occurrences of a primary physiological event based on the data received from the first sensor, identifying and monitoring occurrences of at least one secondary physiological event that is physiologically linked to the primary physiological event, wherein the occurrences of the at least one secondary physiological event are identified based on the data received from the at least one second sensor, establishing a trend of correlation between the primary physiological event and the at least one secondary physiological event during an analysis time period that is divided into discrete time windows, the trend of correlation determined based on event correlation trend data including a number of occurrences of the primary physiological event and each of the at least one secondary physiological events during each of the discrete time windows, wherein the primary physiological event and the at least one secondary physiological event are selected from the group consisting of apnea, bradycardia and oxygen desaturation, presenting the trend of correlation on the display of the clinical monitoring system in real-time via an event correlation trend plot including at least one graph illustrating the trend of correlation between the primary physiological event and the at least one secondary physiological event, and one of increasing and initiating a ventilatory support provided to the patient when a positive trend of correlation is established, wherein the ventilatory support includes one of mechanical ventilation, CPAP and oxygen flow therapy.

10. The clinical monitoring system of claim 9, wherein the computer is configured to identify several different types of secondary physiological events and to establish and present a trend of correlation between the primary physiological event and each of the secondary physiological event types.

11. The clinical monitoring system of claim 10, wherein the computer is configured to categorize identified primary physiological events based on the types of physiologically linked secondary physiological events and to establish the trend of correlation by determining a number of primary physiological events of each category as a function of time.

12. The clinical monitoring system of claim 11, wherein the computer is configured to determine the number of primary physiological events in each category for each of a plurality of discrete time windows.

13. The clinical monitoring system of claim 9, wherein the computer is configured to present the event correlation trend plot in a correlation trend pane on the display, and occurrences of the primary physiological event and occurrences of the at least one secondary physiological event are displayed in an event tracking pane on the display.

14. The clinical monitoring system of claim 13, wherein the event correlation trend plot comprises multiple graphs of different colors or patterns, each illustrating a trend of correlation between the primary physiological event and a respective type of secondary physiological event.

15. The clinical monitoring system of claim 9, wherein the computer is configured to categorize identified primary physiological events based on types of physiologically linked secondary physiological events, and to establish the trend of correlation by determining a number of primary physiological events of each category as a function of time, and the computer is configured to present the event correlation trend data via an event correlation trend plot displayed in a correlation trend pane on the display, wherein the event correlation trend plot comprises at least one graph illustrating the trend of correlation between the primary physiological event and the at least one secondary physiological event, wherein the at least one graph is a distribution graph representing the distribution of different categories of primary physiological events as a function of time, and occurrences of the primary physiological event and occurrences of the at least one secondary physiological event are displayed in an event tracking pane on the display.

16. The clinical monitoring system of claim 9, wherein the primary physiological event is apnea and the at least one secondary physiological event is selected from the group consisting of bradycardia and oxygen desaturation.

17. The clinical monitoring system of claim 9, wherein the primary physiological event is bradycardia and the at least one secondary physiological event is selected from the group consisting of apnea and oxygen desaturation.

18. The clinical monitoring system of claim 9, wherein the physiological parameters are obtained during a period of mechanical ventilation of the patient or a period of continuous positive airway pressure therapy administered to the patient.

19. The clinical monitoring system of claim 9, wherein one of the first sensor and the at least one second sensor includes a respiratory sensor, and the respiratory sensor is selected from the group consisting of a flow sensor, a pressure sensor and an Edi catheter.

20. The clinical monitoring system of claim 9, wherein one of the first sensor and the at least one second sensor includes a heart rate sensor, and the heart rate sensor is selected from the group consisting of an electrocardiogram sensor, an Edi catheter and a pulse oximeter.

21. The clinical monitoring system of claim 9, wherein the computer is further configured to present a ventilation recommendation relating to the treatment of the patient by a breathing apparatus on the display based on the established trend of correlation between the primary physiological event and the at least one secondary physiological event, wherein the display includes an actuation button and one or more ventilation recommendation modification buttons, wherein the one or more ventilation recommendation buttons are actuatable to modify the ventilation recommendation, and the actuation button, when actuated, results in the computer operating the breathing apparatus so as to ventilate the patient in accordance with the ventilation recommendation unless modified by the one or more ventilation recommendation buttons, in which case the actuation button, when actuated, results in the computer operating the breathing apparatus in accordance with the modified ventilation recommendation.

* * * * *